(12) United States Patent
Miesel

(10) Patent No.: US 10,357,620 B2
(45) Date of Patent: Jul. 23, 2019

(54) DETERMINING CATHETER STATUS

(71) Applicant: Medtronic, Inc., Minneapolis, MN (US)

(72) Inventor: Keith A. Miesel, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 770 days.

(21) Appl. No.: 14/860,198

(22) Filed: Sep. 21, 2015

(65) Prior Publication Data
US 2016/0074600 A1  Mar. 17, 2016

Related U.S. Application Data

(60) Division of application No. 12/623,484, filed on Nov. 23, 2009, now Pat. No. 9,138,537, which is a
(Continued)

(51) Int. Cl.
*A61M 5/50* (2006.01)
*A61M 5/168* (2006.01)
(Continued)

(52) U.S. Cl.
CPC ...... *A61M 5/5086* (2013.01); *A61M 5/14276* (2013.01); *A61M 5/16854* (2013.01);
(Continued)

(58) Field of Classification Search
CPC ............ A61M 5/5089; A61M 5/14276; A61M 5/16831; A61M 5/16854; A61M 27/006; A61M 2202/0464
See application file for complete search history.

(56) References Cited

U.S. PATENT DOCUMENTS 3,882,443 A   5/1975   Mortia
4,373,527 A   2/1983   Fischell
(Continued)

FOREIGN PATENT DOCUMENTS

EP   0 248 632   12/1987
EP   0 248 633   12/1987
(Continued)

OTHER PUBLICATIONS

U.S. Appl. No. 11/731,356, filed Mar. 30, 2007, Medtronic, Inc.
(Continued)

*Primary Examiner* — Nathan R Price
*Assistant Examiner* — Anh Bui
(74) *Attorney, Agent, or Firm* — Mueting, Raasch & Gebhardt, P.A.

(57) ABSTRACT

A method for determining the status of a catheter of an implanted infusion system, where the catheter is intended to deliver a fluid composition to CSF of a patient, includes monitoring catheter pressure, developing a pressure modulation profile based on the monitored pressure, and comparing the developed pressure modulation profile to a predetermined pressure profile. The predetermined pressure profile may be a profile of cerebrospinal fluid or a bolus infusion or withdrawal profile for the catheter. A determination of catheter status, such as properly functioning, occluded or leaky, can be made based on the comparison.

20 Claims, 18 Drawing Sheets

Related U.S. Application Data continuation-in-part of application No. 11/731,356, filed on Mar. 30, 2007, now Pat. No. 8,323,244, and a continuation-in-part of application No. 11/778,400, filed on Jul. 16, 2007, now Pat. No. 7,955,319, which is a continuation of application No. 10/836,115, filed on Apr. 30, 2004, now Pat. No. 7,320,676.

(60) Provisional application No. 60/508,020, filed on Oct. 2, 2003.

(51) Int. Cl.
    *A61M 5/142* (2006.01)
    *A61M 27/00* (2006.01)
    *A61M 5/172* (2006.01)

(52) U.S. Cl.
    CPC ...... *A61M 5/16859* (2013.01); *A61M 27/006* (2013.01); *A61M 2005/1726* (2013.01); *A61M 2202/0464* (2013.01)

(56) References Cited

U.S. PATENT DOCUMENTS

| | | | |
|---|---|---|---|
| 4,388,833 A | 6/1983 | Kuwayama | |
| 4,530,696 A | 7/1985 | Bisera | |
| 4,534,756 A | 8/1985 | Nelson | |
| 4,551,133 A | 11/1985 | Zegers de Beyl | |
| 4,619,653 A | 10/1986 | Fischell | |
| 4,710,163 A | 12/1987 | Butterfield | |
| 4,714,462 A | 12/1987 | DiDomenico | |
| 4,784,645 A | 11/1988 | Fischell | |
| 4,979,940 A | 12/1990 | Bobo, Jr. | |
| 5,006,997 A * | 4/1991 | Reich ............... | A61M 5/14276 128/DIG. 12 |
| 5,024,668 A | 6/1991 | Peters | |
| 5,040,536 A | 8/1991 | Riff | |
| 5,059,171 A | 10/1991 | Bridge | |
| 5,078,682 A | 1/1992 | Miki | |
| 5,087,245 A | 2/1992 | Doan | |
| 5,096,385 A | 3/1992 | Georgi | |
| 5,116,203 A | 5/1992 | Natwick | |
| 5,158,547 A | 10/1992 | Doan | |
| 5,176,631 A | 1/1993 | Koenig | |
| 5,190,522 A | 3/1993 | Wojcicki | |
| 5,205,819 A | 4/1993 | Ross | |
| 5,207,666 A | 5/1993 | Idriss | |
| 5,276,610 A | 1/1994 | Maeda | |
| 5,279,544 A | 1/1994 | Gross | |
| 5,290,231 A | 3/1994 | Marcadis | |
| 5,328,460 A | 7/1994 | Lord | |
| 5,336,181 A | 8/1994 | Nakao | |
| 5,342,298 A | 8/1994 | Michaels | |
| 5,356,378 A | 10/1994 | Doan | |
| 5,496,273 A | 3/1996 | Pastrone | |
| 5,501,665 A | 3/1996 | Jhuboo | |
| 5,535,752 A | 7/1996 | Halperin | |
| 5,560,366 A | 10/1996 | Harada | |
| 5,605,545 A | 2/1997 | Nowosielski | |
| 5,609,576 A | 3/1997 | Voss | |
| 5,669,877 A | 9/1997 | Blomquist | |
| 5,695,473 A | 12/1997 | Olsen | |
| 5,800,387 A | 9/1998 | Duffy | |
| 5,827,223 A | 10/1998 | Butterfield | |
| 5,853,386 A | 12/1998 | Davis et al. | |
| 5,893,838 A | 4/1999 | Daoud | |
| 5,899,873 A | 5/1999 | Jones | |
| 5,906,589 A | 5/1999 | Gordon | |
| 5,928,195 A | 7/1999 | Malamud | |
| 5,935,106 A | 8/1999 | Olsen | |
| 6,152,898 A | 11/2000 | Olsen | |
| 6,203,523 B1 | 3/2001 | Haller | |
| 6,213,972 B1 | 4/2001 | Butterfield | |
| 6,241,704 B1 | 6/2001 | Peterson | |
| 6,358,225 B1 | 3/2002 | Butterfield | |
| 6,364,842 B1 | 4/2002 | Amano | |
| 6,394,986 B1 | 5/2002 | Millar | |
| 6,423,029 B1 | 7/2002 | Elsberry | |
| 6,423,035 B1 | 7/2002 | Das | |
| 6,458,102 B1 | 10/2002 | Mann | |
| 6,464,687 B1 | 10/2002 | Ishikawa | |
| 6,485,465 B2 | 11/2002 | Moberg | |
| 6,551,290 B1 | 4/2003 | Elsberry | |
| 6,609,071 B2 | 8/2003 | Shapiro | |
| 6,620,151 B2 | 9/2003 | Blischak | |
| 6,648,821 B2 | 11/2003 | Lebel | |
| 6,716,193 B1 | 4/2004 | Neftel | |
| 6,740,059 B2 | 5/2004 | Flaherty | |
| 6,742,999 B1 | 6/2004 | Nusser | |
| 6,966,325 B2 | 11/2005 | Erickson | |
| 7,022,116 B2 | 4/2006 | Morris | |
| 7,054,782 B2 | 5/2006 | Hartlaub | |
| 7,092,797 B2 | 8/2006 | Gaines | |
| 7,104,763 B2 | 9/2006 | Bouton | |
| 7,118,565 B2 | 10/2006 | Abboud | |
| 7,255,680 B1 | 8/2007 | Gharib | |
| 7,255,683 B2 | 8/2007 | Vanderveen | |
| 7,291,126 B2 | 11/2007 | Shekalim | |
| 7,311,693 B2 | 12/2007 | Shekalim | |
| 7,320,676 B2 | 1/2008 | Miesel | |
| 7,338,464 B2 | 3/2008 | Blischak | |
| 7,437,644 B2 | 10/2008 | Ginggen | |
| 7,452,190 B2 | 11/2008 | Bouton | |
| 7,505,869 B2 | 3/2009 | Hartlaub | |
| 7,621,878 B2 | 11/2009 | Ericson | |
| 2001/0034502 A1 | 10/2001 | Moberg | |
| 2002/0040208 A1 | 4/2002 | Flaherty | |
| 2002/0065471 A1 | 5/2002 | Amano | |
| 2002/0072733 A1 | 6/2002 | Flaherty | |
| 2002/0077581 A1 | 6/2002 | Davidner | |
| 2002/0087115 A1 | 7/2002 | Hartlaub | |
| 2002/0107477 A1 | 8/2002 | Kipfer | |
| 2002/0120236 A1 | 8/2002 | Diaz | |
| 2002/0173773 A1 | 11/2002 | Olsen | |
| 2003/0073954 A1 | 4/2003 | Moberg | |
| 2003/0078547 A1 | 4/2003 | Shekalim | |
| 2003/0088238 A1 | 5/2003 | Poulsen | |
| 2003/0125662 A1 | 7/2003 | Bui | |
| 2003/0135154 A1 | 7/2003 | Heiniger | |
| 2003/0236489 A1 | 12/2003 | Jacobson | |
| 2004/0044305 A1 | 3/2004 | Hughett | |
| 2004/0085215 A1 | 5/2004 | Moberg | |
| 2004/0087894 A1 | 5/2004 | Flaherty | |
| 2004/0127844 A1 | 7/2004 | Flaherty | |
| 2004/0220548 A1 | 11/2004 | Heruth et al. | |
| 2004/0230125 A1 | 11/2004 | Amano | |
| 2004/0260233 A1 | 12/2004 | Garibotto | |
| 2004/0260234 A1 | 12/2004 | Srinivasan | |
| 2005/0075624 A1 | 4/2005 | Miesel | |
| 2005/0090799 A1 | 4/2005 | Morris | |
| 2005/0123420 A1 | 6/2005 | Richter | |
| 2005/0148885 A1 | 7/2005 | Tweed | |
| 2005/0192529 A1 | 9/2005 | Butterfield | |
| 2005/0209512 A1 | 9/2005 | Heruth | |
| 2005/0209513 A1 | 9/2005 | Heruth | |
| 2005/0222643 A1 | 10/2005 | Heruth et al. | |
| 2005/0234514 A1 | 10/2005 | Heruth et al. | |
| 2005/0234518 A1 | 10/2005 | Heruth et al. | |
| 2005/0241387 A1 | 11/2005 | Miesel et al. | |
| 2005/0245858 A1 | 11/2005 | Miesel | |
| 2005/0267413 A1 | 12/2005 | Wang | |
| 2006/0060190 A1 | 3/2006 | Sindberby | |
| 2006/0079793 A1 | 4/2006 | Mann | |
| 2006/0161376 A1 | 7/2006 | Hartlaub | |
| 2006/0271029 A1 | 11/2006 | Abboud | |
| 2007/0060871 A1 | 3/2007 | Istoc | |
| 2007/0078381 A1 | 4/2007 | Yap | |
| 2007/0149926 A1 | 6/2007 | Moberg | |
| 2007/0191770 A1 | 8/2007 | Moberg | |
| 2007/0232936 A1 | 10/2007 | Mann | |
| 2007/0258083 A1 | 11/2007 | Heppell | |
| 2007/0270782 A1 | 11/2007 | Miesel et al. | |
| 2007/0274843 A1 | 11/2007 | Vanderveen | |
| 2008/0009837 A1 | 1/2008 | Miesel | |

(56) References Cited

U.S. PATENT DOCUMENTS

| | | |
|---|---|---|
| 2008/0097287 A1 | 4/2008 | Nelson |
| 2008/0139996 A1 | 6/2008 | Bowman |
| 2008/0167641 A1 | 7/2008 | Hansen |
| 2009/0082757 A1 | 3/2009 | Rogers et al. |
| 2010/0016918 A1 | 1/2010 | Mann |

FOREIGN PATENT DOCUMENTS

| | | |
|---|---|---|
| EP | 0 328 162 | 8/1989 |
| EP | 0 621 791 | 11/1994 |
| EP | 0 522 527 | 12/1994 |
| EP | 0 856 326 | 8/1998 |
| EP | 1 342 481 | 9/2003 |
| EP | 1 535 637 | 6/2005 |
| EP | 0 993 268 | 11/2005 |
| EP | 1 839 695 | 10/2007 |
| EP | 1 592 468 | 9/2008 |
| WO | WO 95/32013 | 11/1995 |
| WO | WO 1999/55225 | 11/1999 |
| WO | WO 00/44420 | 8/2000 |
| WO | WO 2002/064040 | 8/2002 |
| WO | WO 2002/070047 | 9/2002 |
| WO | WO 2005/072792 | 8/2005 |
| WO | WO 2005/089860 | 9/2005 |
| WO | WO 2005/119181 | 12/2005 |
| WO | WO 2006/067217 | 6/2006 |
| WO | WO 2006/108775 | 10/2006 |
| WO | WO 2007/020029 | 2/2007 |

OTHER PUBLICATIONS

U.S. Appl. No. 11/731,355, filed Mar. 30, 2007, Medtronic, Inc.
U.S. Appl. No. 11/778,400, filed Jul. 16, 2007, Medtronic, Inc.
Giepel et al., "Design of an Implantable Active Microport System for Patient Specific Drug Release," Proceedings of the 24$^{th}$ IASTED International Multi-Conference on Biomedical Engineering (The International Association of Science and Technology for Development), Feb. 15-17, 2006, Innsbruck, Austria; pp. 161-166.
"The SynchroMed Pump" datasheet, [online], Medtronic, Inc., Minneapolis, MN, Version b3.01, [retrieved Oct. 19, 2007]. Retrieved from the Internet at <URL:http://www.medtronic.com/neuro/paintherapies/pain treatment ladder/drug infusion/pumps pump sel/synchromed pumps:html>, 4 pgs.

\* cited by examiner

A)

B)

DETERMINING CATHETER STATUS

RELATED APPLICATIONS

The application is a divisional patent application of U.S. patent application Ser. No. 12/623,484, filed on Nov. 23, 2009 and issuing as U.S. Pat. No. 9,138,537 on Sep. 22, 2015, which is a continuation-in-part application of (i) U.S. patent application Ser. No. 11/731,356, filed on Mar. 30, 2007, now U.S. Pat. No. 8,323,244, and (ii) U.S. patent application Ser. No. 11/778,400, filed on Jul. 16, 2007, now U.S. Pat. No. 7,955,319, which is a continuation of U.S. patent application Ser. No. 10/836,115 filed on Apr. 30, 2004, now U.S. Pat. No. 7,320,676, which claims priority to U.S. Provisional Application No. 60/508,020, filed on Oct. 2, 2003, which patents and applications are hereby incorporated herein by reference in their respective entireties to the extent that they do not conflict with the present disclosure

FIELD

The present disclosure relates generally to systems and methods for identifying malfunctions in an implanted catheter of an infusion system by sensing fluid pressure.

BACKGROUND

More than 100,000 individuals worldwide are implanted with an infusion system configured to deliver therapeutic agent to the cerebrospinal fluid (CSF) of a patient. Such systems typically have a reservoir containing a supply of therapeutic substance awaiting delivery to the patient's CSF. A pump may be fluidly coupled to the reservoir for creating fluidic pressure to facilitate delivery of the therapeutic substance. A catheter provides a pathway for delivering the therapeutic substance to the CSF of the patient. All parts of the infusion system need to operate adequately to ensure proper delivery of therapeutic substances using the system.

While perhaps the least complex component of an infusion system, catheters can have operational problems or can develop operational problems. For example, catheters may be placed in the wrong location when originally deployed or the catheters may move (migrate) over time such that fluids (e.g., therapeutic substances) delivered through the catheters are not delivered to the originally intended delivery site (e.g., a CSF compartment).

Catheters can also become obstructed or clogged during use. A partial or complete blockage could prevent an adequate supply of the therapeutic substance from reaching the intended delivery site of the patient.

Catheters can also leak due to cuts, tears, etc. A leak, small or large, can also prevent some or all of the therapeutic substance from reaching the selected internal delivery site of the patient and may result in therapeutic substance being delivered to unintended sites, which may create further issues.

Some infusion systems have been proposed which include pressure sensors capable of monitoring pressure in the catheter to determine whether a catheter malfunction has occurred. However, to date, methods and systems for determining catheter status of the more than 100,000 already implanted infusion devices that deliver agents to a patient's CSF, where the methods and systems employ pressure sensors external to the device or patient, have been lacking

SUMMARY

This disclosure, among other things, describes systems and methods that allow for determination of catheter status in implanted medical systems in which the catheter is intended to deliver therapeutic agent to a target region of a patient, such as the CSF. The systems and methods, in various embodiments, employ a probe that may be inserted percutaneously into a patient to be placed in fluid communication with an implanted catheter. The probe, such as a needle, has a lumen that can be fluidly coupled with the catheter and a pressure sensor, which may be external to the patient. Thus, the systems and methods described herein can be used to monitor the status of a catheter associated with in an implanted infusion system that does not have an on-board pressure sensor.

In various embodiments, the methods and systems described herein take advantage of characteristic CSF pressure profiles that can be transmitted via the implanted catheter. As described herein, such characteristic pressure profiles can be detected by an external pressure sensor operably coupled to a probe, such as a needle, having a lumen in fluid communication with the implanted catheter. A pressure profile may be developed based on the pressure monitored via the external sensor, which can then be compared to a predetermined pressure profile for one or more physiological parameters. For example, if the developed profile is indicative of a characteristic CSF pressure profile based on respiration and heart rate is detected by the pressure sensor, the catheter is likely to be properly positioned in the CSF and operating properly. If a characteristic CSF pressure profile is not detected by the pressure sensor, there is likely a catheter malfunction, such as an occlusion, leak, or catheter migration.

In various embodiments, the methods and systems described herein take advantage of intracatheter pressure profiles generated by infusion of fluid boluses through the catheter. Bolus infusions of fluid into a catheter result in characteristic pressure profiles in occluded catheters, catheters that have leaks, and catheters that are free of leaks and occlusions. These characteristic bolus profiles can be measured by the pressure sensor coupled to the probe in communication with the catheter. Accordingly, a bolus of fluid may be infused into the catheter; e.g. via the infusion device, and pressure may be measured to determine whether the pressure exhibits a characteristic bolus profile of an occluded catheter, a catheter having a leak, or a normally functioning catheter. In some embodiments, fluid is withdrawn from the catheter to monitor catheter status. Withdrawal of fluid from the catheter can generate characteristic profiles similar to those generated by bolus infusions.

In various embodiments, a system for determining the status of a catheter of an implanted infusion system includes a probe having a lumen defining an inner diameter. The inner diameter of the probe is 60% or less than 60% of the diameter of the catheter. The system also includes a tube operably coupled to the probe. The tube has a lumen defining an inner diameter. The inner diameter of the probe is 60% or less than 60% of the inner diameter of the tube. The system further includes a pressure sensor operably coupled to the tube and configured to measure pressure in the lumen of the tube. Despite the difference in inner diameter between the probe and the tube, the pressure sensor is capable of detecting a subtle change in pressure characteristic of a CSF pressure profile.

One or more embodiments of the methods or systems described herein provide one or more of benefits relative to existing methods or systems for monitoring or determining the status of an implanted catheter. For example, embodiments of the methods or systems described herein provide a mechanism for determining catheter status in the over 100, 000 patients already implanted with infusion systems configured to deliver therapeutic agents to cerebrospinal fluid of the patients. That is, proposals to include pressure sensors on board implantable infusion devices are of little use for monitoring catheter status in patients who already have an infusion device without such technology implanted. Further, because embodiments of the methods and systems described herein employ a probe that can be percutaneously placed in fluid communication with an implanted catheter, catheter pressure can be monitored via the probe external to the patient, which can provide several advantages relative to incorporating the pressure sensor in the implantable infusion device. For example, the power requirements of the implantable device can be reduced if the device power source is not drained by monitoring catheter pressure. Further processing power than may be employed to run algorithms to determine whether the monitored pressure is indicative of a malfunction can be spared by performing the monitoring by an external device. These and other advantages will be apparent to those of skilled in the art upon reading the following detailed description.

BRIEF DESCRIPTION OF THE DRAWINGS

The accompanying drawings, which are incorporated into and form a part of the specification, illustrate several embodiments of the present disclosure and, together with the description, serve to explain the principles of the disclosure. The drawings are only for the purpose of illustrating embodiments of the disclosure and are not to be construed as limiting the disclosure.

The schematic drawings presented herein are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to."

The present disclosure relates to, among other things, systems and methods that allow for detection of catheter status in implanted medical systems in which the catheter is intended to deliver therapeutic agent to the CSF of a patient. The systems and methods can be used to determine the status of a catheter implanted in a patient, where the catheter is coupled to an infusion device that does not have an on-board pressure sensor. Accordingly, the systems and methods described herein provide a way to monitor catheter status of infusion systems already implanted in more than 100,000 people.

Figure 1:
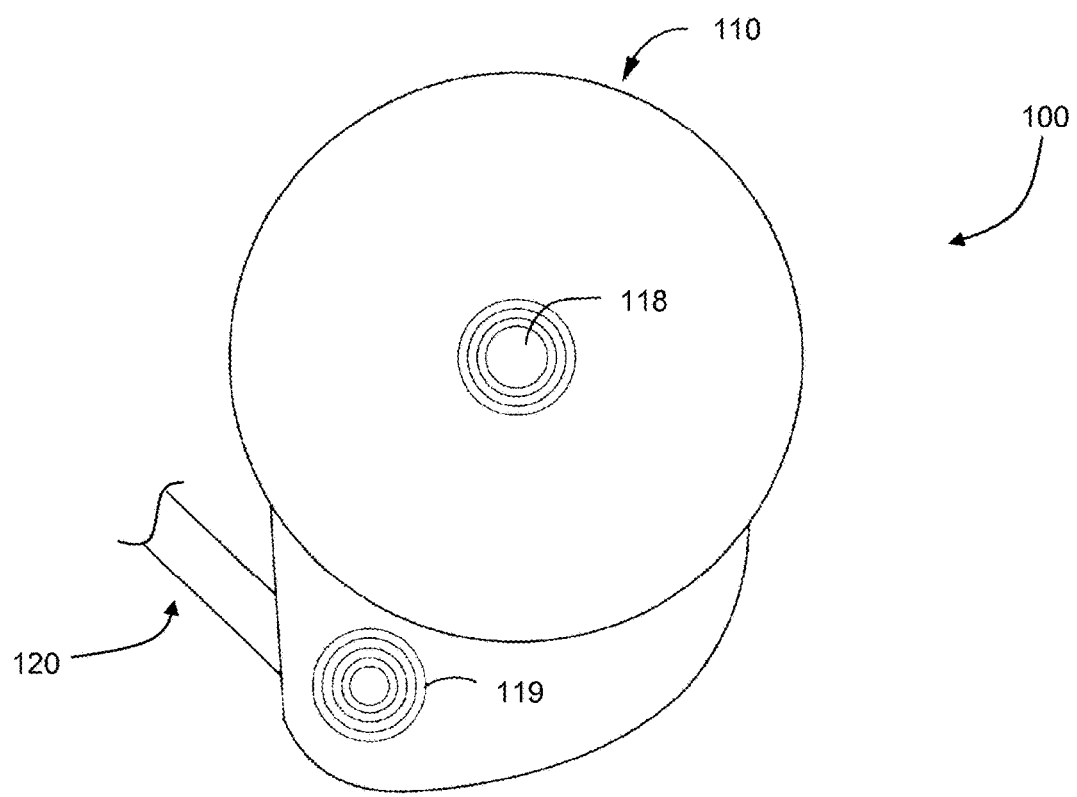
FIG. 1 is a schematic drawing of an embodiment of an implantable infusion system
Figure 2:
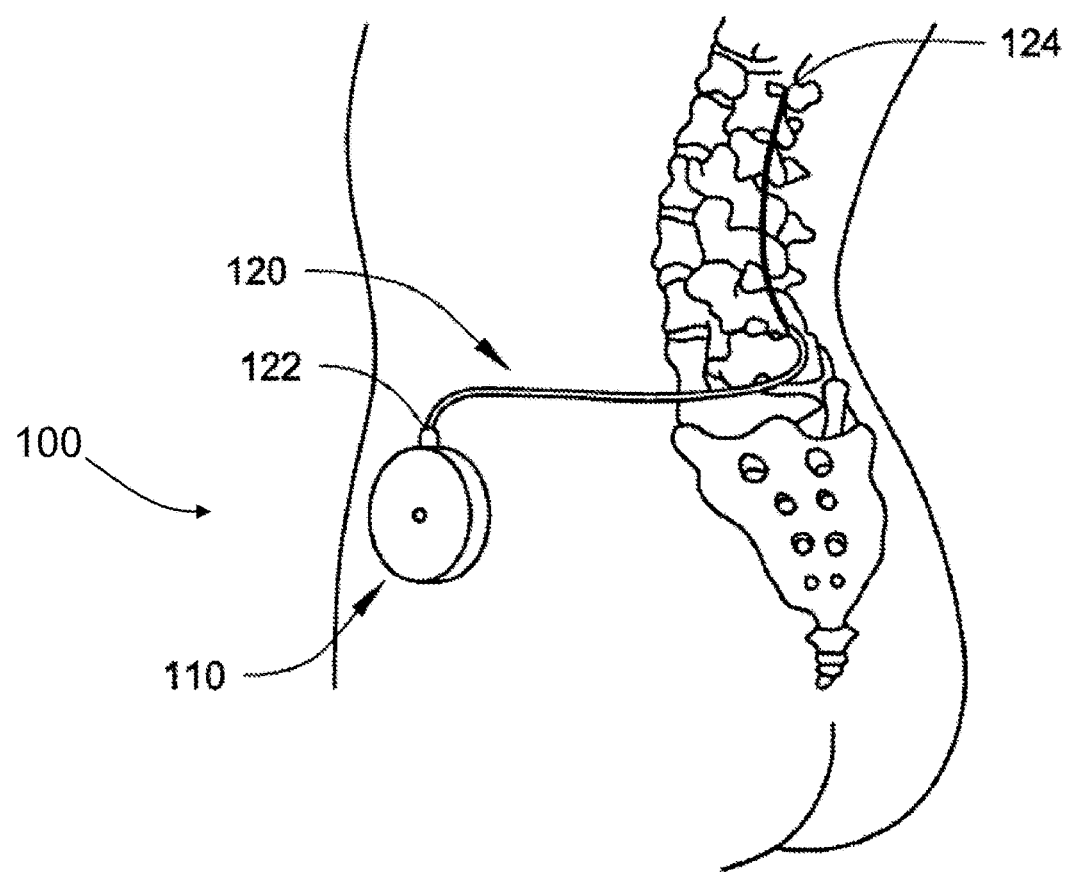
FIG. 2 is a schematic drawing depicting an embodiment of an implanted infusion device.

The methods and pressure monitoring systems described herein may be employed with any suitable implantable infusion system. FIGS. 1-2 show examples of infusion systems 100 with which pressure monitoring systems 300 and methods described herein may be used. The infusion system depicted in FIG. 1 includes an infusion device 110, a catheter 120, and a catheter access port 119 in fluid communication with the catheter 120. The infusion device 110 also includes a refill port 118 in communication with a reservoir for containing therapeutic agent (not shown) disposed within the housing of the device 110. The infusion device 110 may include any suitable mechanism or structure capable of delivering one or more fluids to a patient. The structures used to drive fluids in the infusion devices may be powered (e.g., piston pumps, diaphragm pumps, peristaltic pumps, etc.), may be activated based on pressure to drive fluid out of a reservoir (e.g., using collapsing diaphragms, expanding bladders, etc.), or the like. Examples of some potentially suitable pump assemblies may include, e.g., commercially available implantable infusion pumps such as, for example, the SYNCHROMED II and EL pumps, manufactured by Medtronic, Inc., Minneapolis, Minn.

The infusion system 100 depicted in FIG. 2 is shown implanted in a patient. The infusion system 100 includes an infusion device 110 and catheter 120 having a proximal end 122 attached to the infusion device 110. The infusion device 110 may be surgically implanted in any suitable location, such as subcutaneously in the pectoral, abdominal or other region of the subject's body. The distal end 124 of the catheter 120 is implanted in a patient such that the distal end 124 is located at the selected internal delivery site in the patient (in the intrathecal space of the patient as depicted in FIG. 2, the cerebroventricles, or elsewhere as desired). While not shown in FIG. 2, it will be understood that the depicted infusion device 100 may include a catheter access port in fluid communication with the catheter 120 as described above with regard to FIG. 1.

Figure 3:
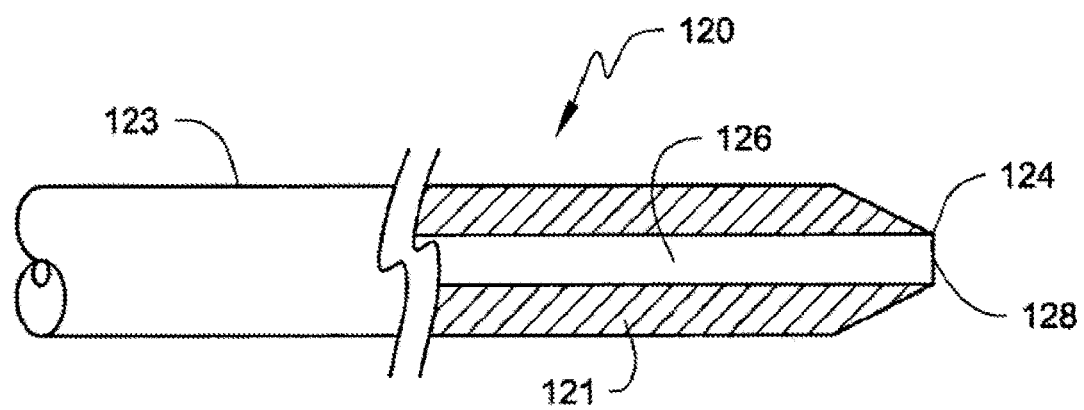
FIG. 3 is a schematic drawing of an enlarged partial cross section of an embodiment of a catheter.

FIG. 3 depicts a portion of a catheter 120 in an enlarged cross-sectional view. The catheter 120 includes an elongated tubular portion 123 that preferably extends from the proximal end (not shown) to the distal end 124. The catheter 120 depicted in FIG. 2 includes a lumen 126 that terminates at opening 128 (or delivery region) at the distal end 124. Therapeutic substances (or other fluids) delivered from the pump assembly 110 to the catheter 120 pass through lumen 126 and preferably exit the catheter 120 through opening 128.

The body of catheter 120 may be constructed of any suitable material, e.g., an elastomeric tube. Examples of some suitable materials include, but are not limited to, silicone rubber (e.g., polydimethyl siloxane) or polyurethane, both of which can provide good mechanical properties and are very flexible. Suitable materials for the catheter 120 are also preferably chemically inert such that they will not interact with therapeutic substances, body tissues, or body fluids while implanted in the patient.

Where the catheter is to be used for intrathecal fluid delivery, it may be preferred that at least a portion of the catheter 120 be sized to fit in the gap between the spinal cord and the dura within the intrathecal space. Catheters intended for delivering fluids to other internal delivery sites will be sized appropriately for those locations. As another consideration in sizing the catheter, the diameter of the lumen 126 is preferably large enough to accommodate expected infusion rates with acceptable flow resistance. The wall 121 of the catheter 120 is preferably thick enough to withstand normal handling during the implant procedure and forces from body tissues during normal motion. As an example, a catheter intended for use in intrathecal fluid delivery may have an outside diameter of 1.25 millimeters (mm), an inside diameter of 0.5 mm, and a wall thickness of 0.375 mm. Such a catheter may have a length of, e.g., 50 centimeters (cm) long to reach from, e.g., a drug infusion pump implanted in the patient's abdomen to the spine.

Although the opening 128 through which the fluid exits the catheter 120 is depicted as a simple opening in the distal end 124 of catheter 120, such an opening 128 is only one embodiment of an infusion section that may be used in connection with the teachings presented herein. Other embodiments of infusion sections may include, e.g., multiple openings, permeable membranes, or the like. Although the infusion section (opening 128) of the depicted catheter 120 is located at the distal end 124 of the catheter 120, the infusion section(s) may be positioned at any location along the length of the catheter 120 that can be used to deliver the fluid to the selected internal delivery site.

Because physiological pressure modulations at the selected internal delivery site are preferably transmitted into the fluid located within the lumens of catheters in various embodiments, the construction of the infusion sections is preferably selected to provide for that pressure transmission. In other words, the infusion sections are preferably capable of transmitting physiological pressure modulations (e.g., from the CSF where the infusion sections may be located) into the fluid located within the catheter lumen.

Figure 4:
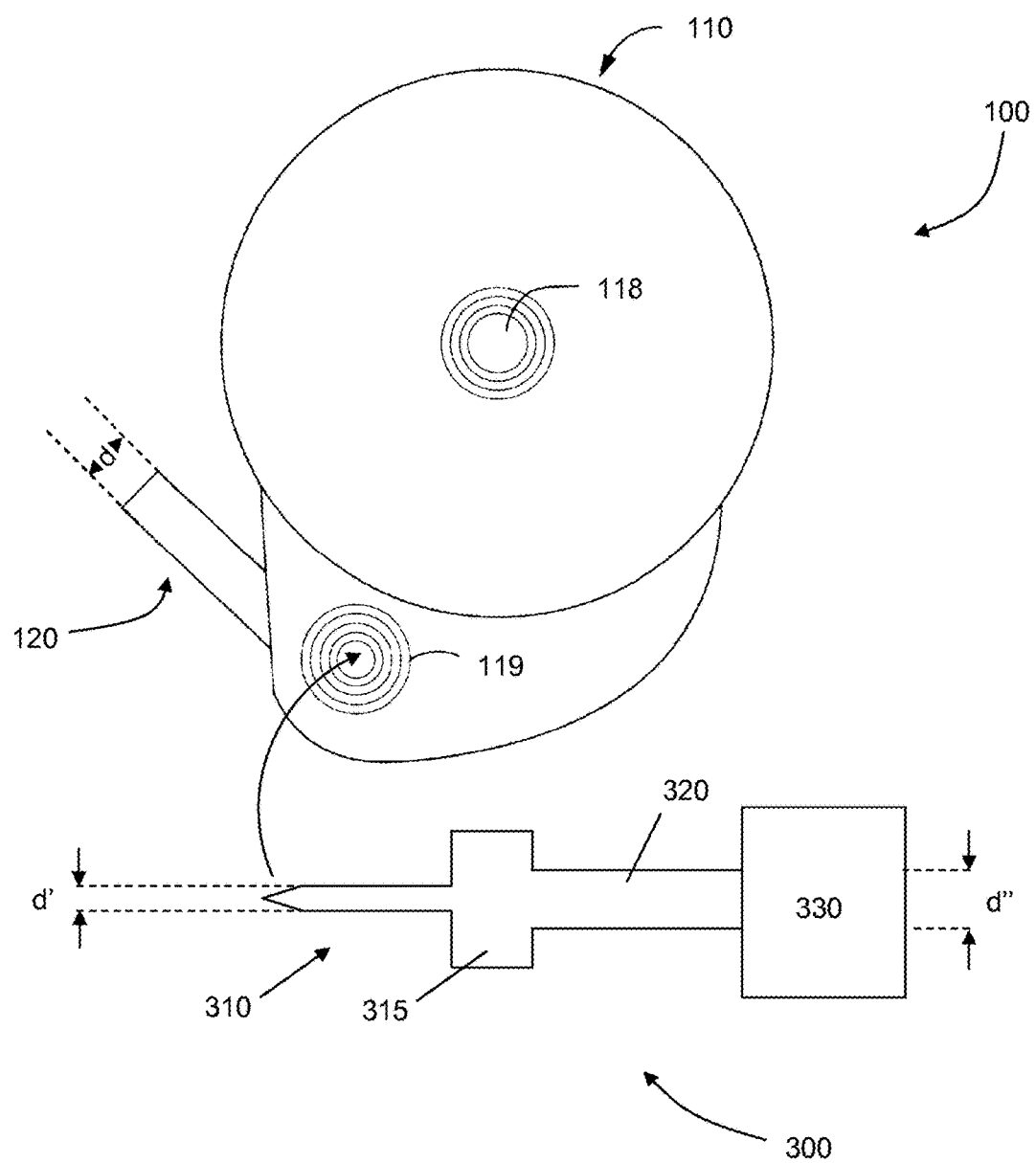
FIG. 4 is a schematic drawing of an embodiment of a pressure monitoring system and an embodiment of an implantable infusion system.

Referring now to FIG. 4, a system for external monitoring intracatheter pressure to a patient is shown. In the depicted embodiment, a pressure monitoring system 300 and an implantable infusion system 100 are shown. The pressure monitoring system includes a probe 310 that can be inserted transcutaneously into the catheter access port 119 of the infusion system such that a lumen of the probe 310 is placed in communication with the catheter 120. The probe 119 may contain an adaptor 315, such as a leur-type adaptor, to couple the probe to tube 320, having a lumen in communication with a pressure sensor 330. While not shown, it will be understood that the pressure sensor 330 may be coupled to connector 315 without intervening tubing 320 or may be integrated within probe 310, such as in the hub of a needle. In other words, the pressure sensor 330 may be operably coupled to the probe 310 in any suitable manner. Thus, when the probe 310 is properly inserted into the port 119, pressure changes in the catheter can be measured by the pressure sensor 330. Any suitable pressure transducer or sensor 330 may be employed.

The pressure sensor 330 may be adapted or configured to read either gauge or absolute pressure of the fluid in the lumen of the catheter 120. Because the methods described below rely on comparison of pressure modulation profiles, changes in ambient pressure may be of limited importance in implementing the methods because ambient pressure changes can typically be expected to exert the same influence on fluid in the catheter lumen as it does at the selected internal delivery site (e.g., on the CSF in the intrathecal space).

The probe 310 has an inner diameter d' that, in some embodiments, is less than 60% of the inner diameter d of the catheter 120 and is less than 60% of the inner diameter d" of the tube 320. Even with such changing inner diameters, pressure changes in the catheter indicative of a CSF pressure profile are capable of being detected by the external pressure sensor 330.

Tubing 320 may be of any suitable material, such as the materials described above with regard to the catheter. The tubing 320 may have any suitable dimensions, such as an inner diameter of about 0.5 millimeters or greater. The tubing 320 may be of any suitable length, such as a length that allows a desired distance between the probe 310 and the pressure sensor 330.

Figure 5:
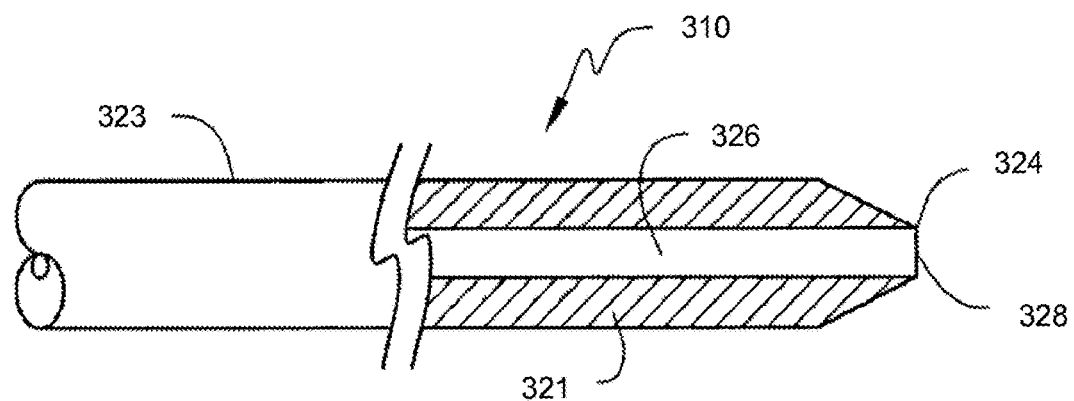
FIG. 5 is a schematic drawing of an enlarged partial cross section of an embodiment of a probe.

Referring now to FIG. 5, an enlarged partial cross-sectional view of a probe 310 is shown. The probe 310 includes an elongated tubular portion 323 that preferably extends from the proximal end (not shown) to the distal end 324. The probe 310 depicted in FIG. 4 includes a lumen 326 that terminates at opening 328 at the distal end 324. Thus, when the distal end 324 is inserted into a catheter access port, the lumen 326 of the probe 310 is placed in fluid communication with the catheter.

The body of probe 310 may be constructed of any suitable material, e.g., rigid metallic material or a rigid plastic. The material should be sufficiently stiff that is can be inserted transcutaneously into a catheter access port without compromising the integrity of the lumen. Examples of suitable materials include stainless steel and titanium. In various embodiments, the inner diameter of the probe, as defined by the lumen 326, is less than 0.35 millimeters. In many embodiments, the probe is a 24-gauge or higher-gauge needle. For many catheter access ports of implantable infusion systems, needles of a gauge less than 24 gauge are too large of an outer diameter to be inserted into the port.

Figure 6:
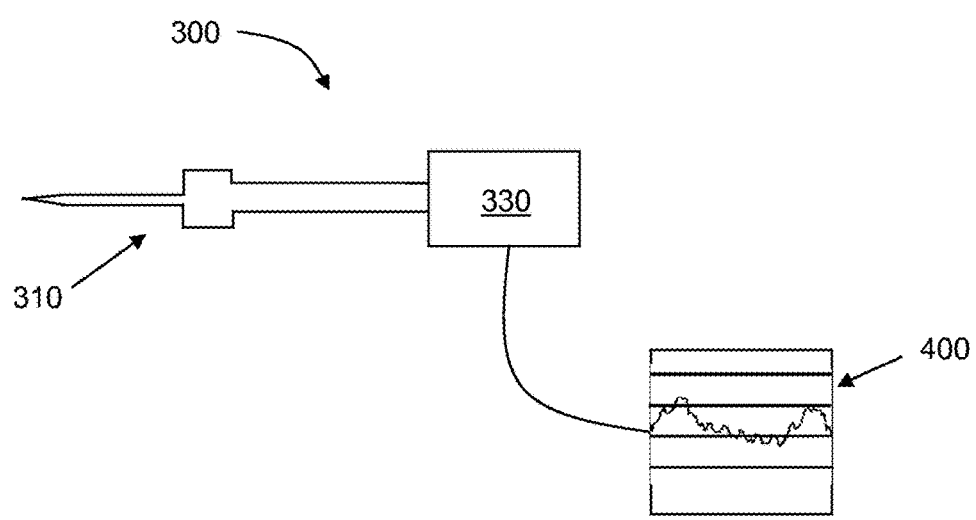
FIG. 6 is a schematic block drawing of an embodiment of a pressure monitoring system operably coupled to a monitor for displaying a pressure profile.

Referring now to FIG. 6 an external pressure monitoring system 300 may include a monitor 400 for displaying pressure profiles. The pressure profiles displayed may be pressure profiles developed from the pressure measured via pressure sensor 330, may be pressure profiles of characteristic CSF pressure profiles or bolus profiles, which are discussed in more detail below, or the like. The system may also include a processor that allows conversion of the measured pressure data into the displayed pressure profile. A possessor may also be employed to compare the developed pressure profiles to characteristic CSF or bolus profiles to assist in determining whether the profiled developed from the measured pressures have characteristics indicative or not indicative of a CSF or bolus profile.

The pressure monitoring system may also communicate with a second device via wires or wirelessly, such as via Bluetooth, USB, serial, or the like, to transmit raw or processed pressure information to the second device capable. The second device or a tertiary device operably coupled to the second device is capable of displaying the pressure information. The second device may be a physician programmer, patient programmer, computer, or the like.

Referring now to FIGS. 7-10, various alternative embodiments of pressure monitoring systems 300 are shown. The systems 300 shown in FIGS. 7-8 include a probe 310 fluidly coupled to tubing 320 via a connector 315 in communication with a pressure sensor 330, e.g., as described above with regard to FIG. 4. The system further includes a tubing 322, which may be the same or different than tubing 320. The tubing 322 is in communication with a bolus delivery apparatus 350, capable of delivering a bolus of infusate through probe 310 and into a catheter of an implantable infusion system when the probe is inserted into a catheter access port of an infusion device (see, e.g., FIG. 4). Pressure within the catheter may be measured via pressure sensor 330 following infusion of the bolus to determine whether pressure profiles characteristic of a properly functioning catheter, a leaky catheter or an occluded catheter is produced, e.g. as described below in more detail.

Figure 7:
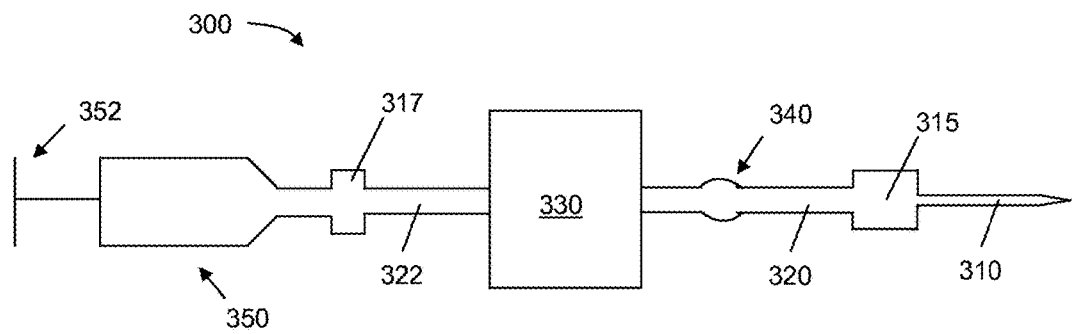
FIGS. 7-8 are schematic illustrations of embodiments of pressure monitoring systems.

In FIG. 7, the bolus delivery apparatus 350 includes a plunger 352 that can be manually depressed to deliver a bolus of fluid from the apparatus 350 through the probe 310. The bolus delivery apparatus is operably coupled to tubing 322 via a connector 317, which may be similar to connector 315 as discussed above with regard to FIG. 4. The bolus delivery apparatus 350 depicted in FIG. 8 includes an automated external pump, such as a piston pump, a peristaltic pump, or the like, to deliver controlled amounts of fluid in controlled amounts of time. One suitable pump than may be used is a Harvard pump.

Figure 8:
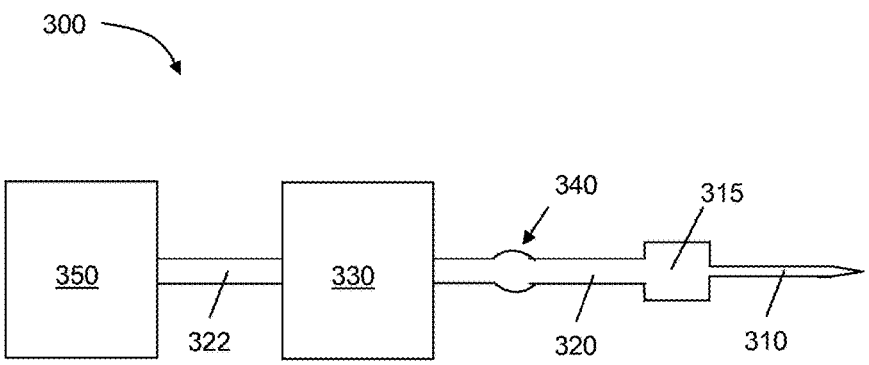

The systems 300 depicted in FIGS. 7-8 include clamp 340 disposed about tubing 320. The clamp 320 may be used in conjunction with the bolus delivery apparatus 350 to withdraw a bolus of fluid from a catheter with which the probe 310 is in communication. The clamp may be located about the tubing 320 at any suitable location. Generally, locating the clamp 320 further from the probe 310 results in lower amounts of fluid delivered. If the fluid delivered contains a therapeutic agent, it may be desirable to minimize the incremental amount of therapeutic agent delivered by positioning the clamp 320 away from the probe 330. The bolus delivery apparatus 350, such as the syringe depicted in FIG. 7, may be activated to deliver or withdraw fluid, e.g. by pushing or pulling the plunger 352, until an appropriate reading is observed or detected by pressure sensor 330, e.g. a pressure change of 1 psi or −1 ppsi. A stop cock (not shown) or other mechanism may be used to close the connection between the bolus delivery apparatus 350, the sensor 330 and the tubing 320. It may be desirable to verify that the sensor 330 still reads at the desired pressure, e.g. 1 psi or more above ambient pressure. The clamp 340 may then be quickly released, transferring the pressure or vacuum to the probe 310 and subsequently to the catheter fluid. The pressure decay back to baseline may be monitored via sensor to determine whether the catheter is properly functioning, e.g. as described in more detail below. Of course, any other suitable method or mechanism for withdrawing a bolus of fluid may be employed.

Figure 9:
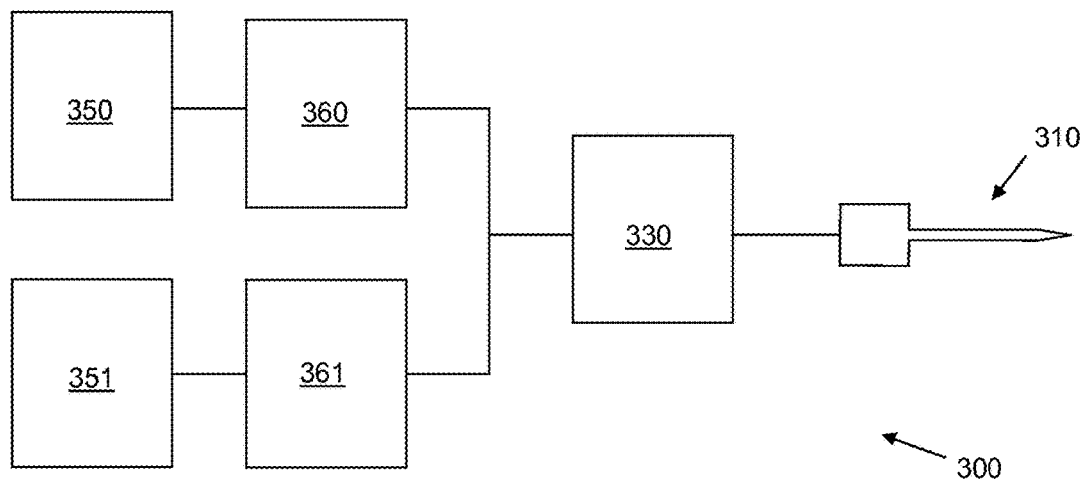
FIGS. 9-10 are schematic block drawings of embodiments of a pressure monitoring systems.

For example and with reference to FIG. 9, an alternative embodiment of a pressure monitoring system 300 capable of delivering or withdrawing a bolus of fluid is shown. The depicted system 300 includes a first 350 and second 351 pumps and first 360 and second 361 valves fluidly coupled to a lumen of the probe 310. The first pump 350 is configured to deliver a bolus of fluid through the probe when optional valve 360 is open. The second pump 351 is configured to withdraw fluid via the probe 310 when optional valve 361 is open. Use of such pumps 350, 351 can allow for precise amounts of fluid to be delivered or withdrawn from the probe 310 providing the ability to accurately determine whether a catheter, with which the probe is in fluid communication, has a leak or occlusion. Of course other suitable configurations, such as a pump capable of pumping fluid in both directions, may be used.

Figure 10:
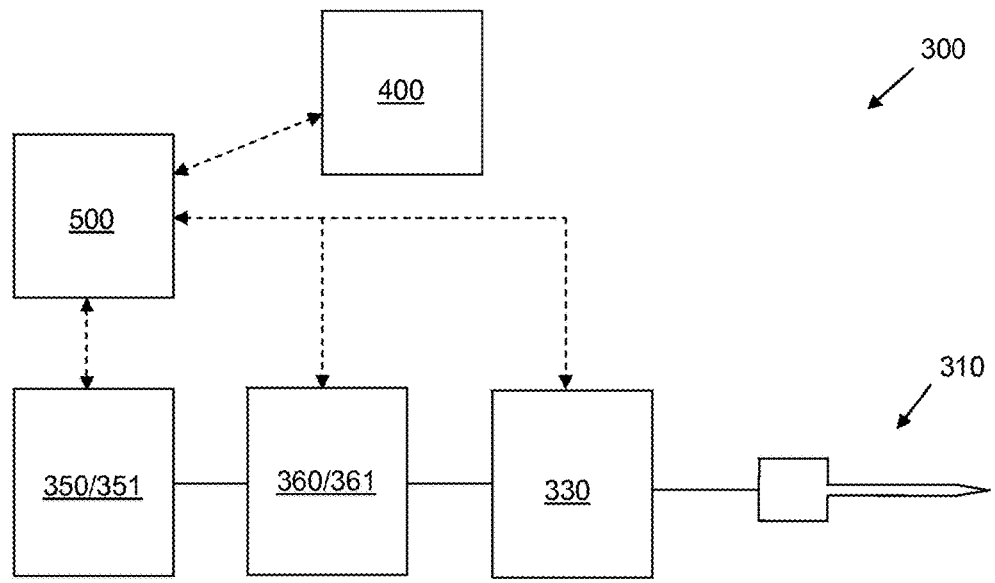

As shown in FIG. 10, a processor 500 may be used to control the pumps 350/351, valves 360/361, or pressure sensor 330 to provide greater precision and accuracy of the system 300. The processor 500 may be operably coupled to a monitor 400 for displaying monitored pressure profiles, e.g. as discussed above with regard to FIG. 6.

As mentioned above, one way to determine the underlying cause of a catheter malfunction is to deliver or withdraw a bolus of fluid into or from the catheter and monitor the resulting pressure profile following the bolus. Any suitable bolus may be delivered over any suitable amount of time, provided that a characteristic profile can be measured. In some embodiments, e.g. where the implantable infusion device to which the catheter is connected includes a programmable pump, the pump may be programmed to deliver a bolus of fluid and the resulting pressure and pressure decay profile may be observed via an appropriate pressure monitoring system, such as the system depicted in FIG. 4. Alternatively, a system as depicted in, for example, FIGS. 7-10 may be employed to deliver or withdraw a bolus of fluid. In many cases, use of an external system to deliver or withdraw the bolus may allow for greater displacement of fluid, resulting in greater pressure changes that may allow for more accurate evaluation of catheter status. Any suitable fluid, such as therapeutic fluid, water, saline, artificial cerebrospinal fluid, or the like may be delivered as the bolus.

Figure 11:
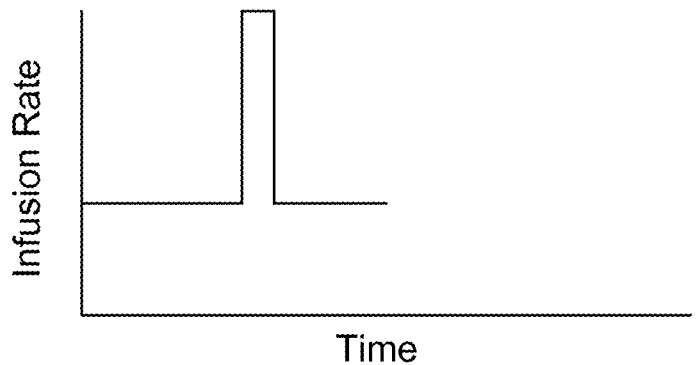
FIG. 11 presents schematic drawings of a graph of infusion rate into a catheter over time (Panel A) and of graphs of intracatheter pressure (Panel B) following the bolus infusion depicted in Panel A. The curves correspond to an occluded (O), a leaky (L), and a normally functioning (N) catheter.
Figure 11:
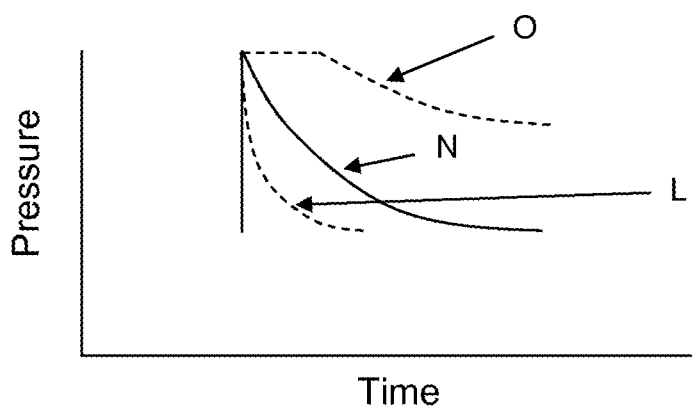

Referring now to FIG. 11, schematic drawings showing hypothetical plots of infusion rate versus time (A) and intracatheter pressure versus time (B) are shown. The time (x-axis) in FIG. 11 (Panels A and B) are simultaneous. As a bolus is delivered (FIG. 11 Panel A), pressure in a properly functioning catheter transiently increases and returns to baseline following a characteristic decay profile (see curve N). In an occluded catheter (curve O), the pressure may (but does not necessarily) increase beyond the maximum pressure observed in a normally functioning catheter free from leaks an occlusions, and has a characteristically slower decay rate than a normal functioning catheter. In a catheter having a leak (curve L), the decay rate (time and profile, by which pressure returns to baseline) is characteristically faster than in a properly functioning catheter. It is notable that the differences in the profiles between occluded, leaky, and properly functioning catheters are detectable in catheters that do not have flow restrictors or valves, which are lacking in most of the currently implanted catheters that are part of an implanted infusion system. The extent of the change in profile in an occluded (O) or leaky (L) catheter relative to a properly functioning catheter (N) will vary depending on the extent of the occlusion (e.g., partial vs. full) or leak (e.g., small vs. large). Some partial occlusions or small leaks may not be readily detectable. However, such leaks and occlusions may not be of therapeutic significance.

In addition, it will be understood that the differences in intercatheter pressure profiles between occluded (O), leaky (L), and properly functioning (N) catheters will be amplified or attenuated depending on the amount of fluid introduced into the catheter in the bolus, as well as the rate the bolus is delivered to the catheter. Characteristic pressure profiles can be generated empirically, theoretically or otherwise for a given catheter of a given length with a given bolus delivered at a given rate. The rates and bolus amounts can be varied to achieve a variety of profiles that may be used to determine whether the observed profile in an implanted catheter is that of a properly functioning catheter, an occluded catheter (possible increase in maximal pressure or slower decay rate) or of a leaky catheter (possible decrease in maximal pressure and faster decay rate).

Figure 12A:
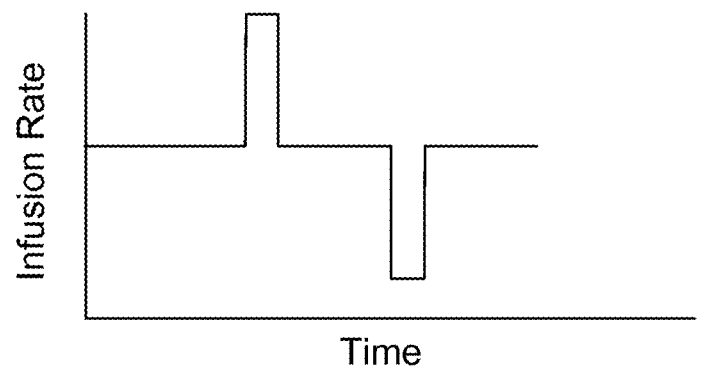
FIG. 12A is a schematic drawing of a graph of infusion rate into a catheter over time.
Figure 12B:
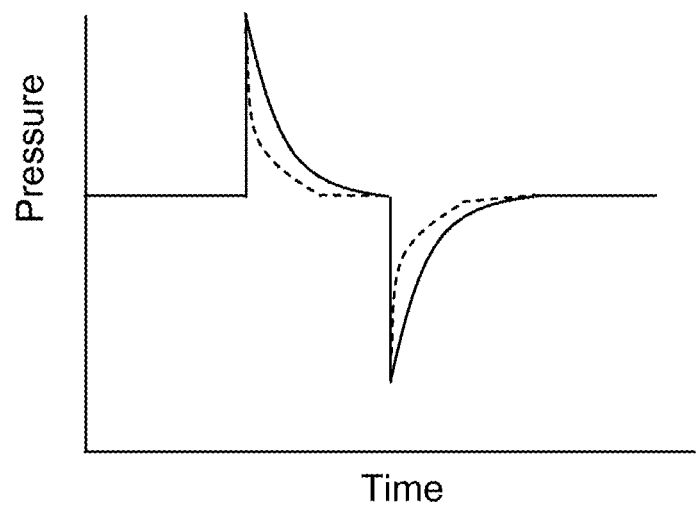
FIG. 12B is a schematic drawing of graphs of intracatheter pressure following the infusion depicted in FIG. 12A. The curves correspond to a leaky (dashed lines), and a normally functioning (solid lines) catheter.
Figure 12C:
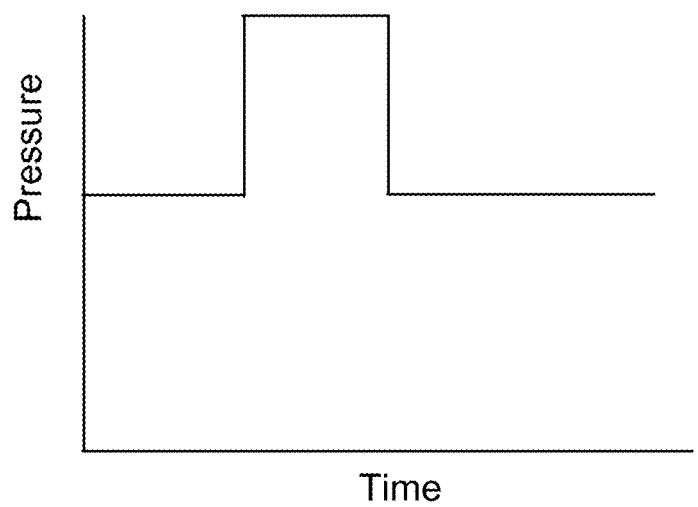
FIG. 12C is a schematic drawing of a graph of intracatheter pressure following the infusion depicted in FIG. 12A. The curve corresponds to an occluded catheter

Referring now to FIGS. 12A-C, schematic drawings showing hypothetical plots of infusion rate versus time (A) and intercatheter pressure versus time (B,C) are shown. The time (x-axis) in FIGS. 12A-C are simultaneous. As shown in FIG. 12A, delivery of a bolus of fluid is followed by withdrawal of a bolus of infusion (or vice-versa). Representative resulting pressure profiles for a properly function catheter (solid lines) and a leaky catheter (dashed lines) are shown in FIG. 12B. The pressure decay rate of a leaky catheter is expected to be faster than the decay rate of a non-leaky catheter. In FIG. 12C, a representative resulting pressure profile of a fully occluded catheter is shown. The pressure increases as fluid a bolus is infused into the blocked catheter until it reaches a maximum and returns to baseline upon withdrawal of the same amount of fluid that was introduced via the initial bolus.

The pressure profiles depicted in FIGS. 11-12 are shown for purposes of illustration. It will be understood that the pressure profiles observed n practice may vary from those depicted. However, regardless of the profile, the characteristics of a leaky, occluded, or properly function catheter may be detected and may be transmitted via a transcutaneously inserted probe in placed communication with the implanted catheter.

Figure 13:
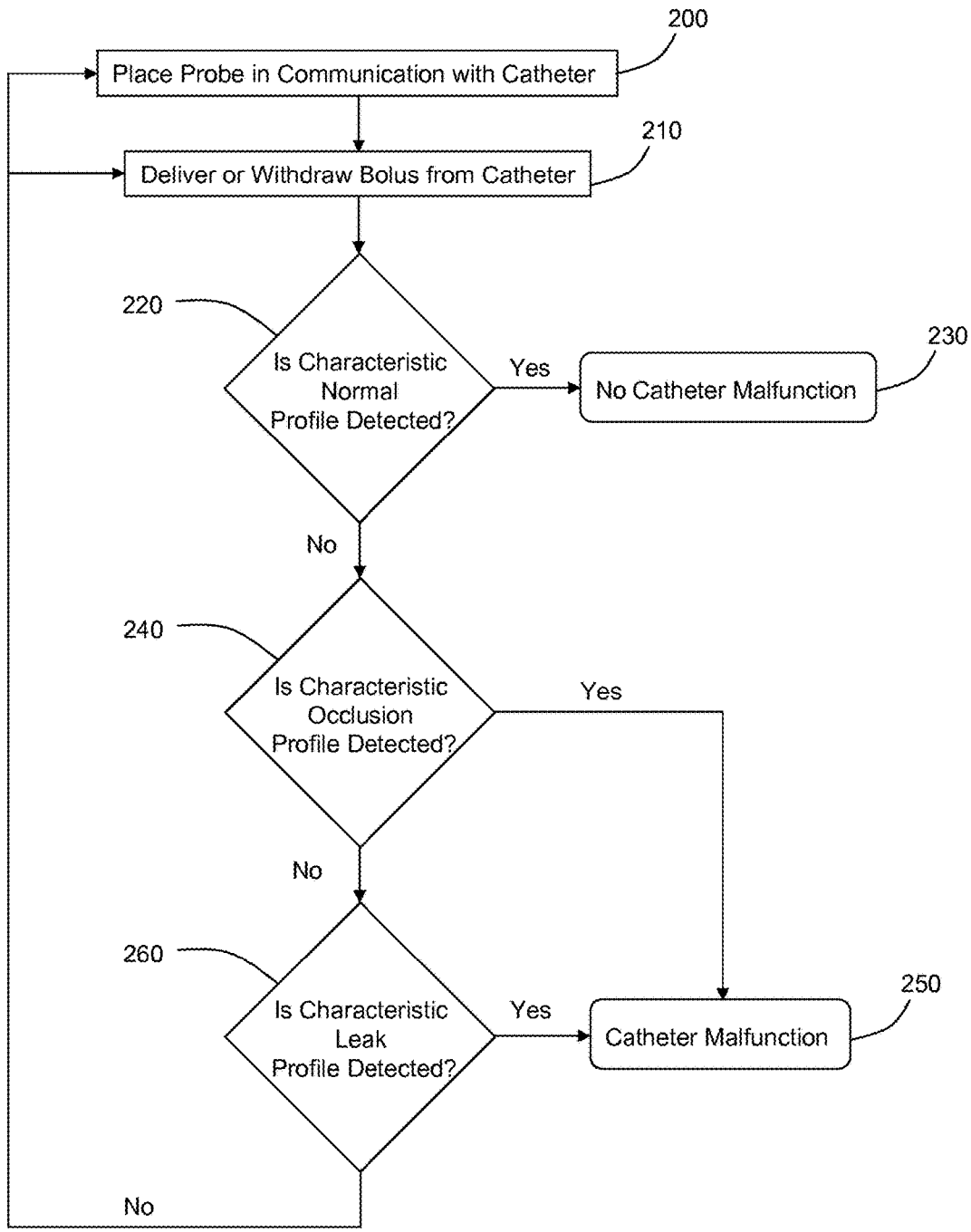
FIG. 13 is a flow diagram providing an overview of an embodiment of a method described herein.

Referring now to FIG. 13 an overview of a method in accordance with one embodiment of the disclosure is depicted. The method includes placing a probe in communication with an implanted catheter (200), e.g. via inserting the probe into a catheter access port of an infusion device to which the catheter is connected (see e.g. FIG. 4). A bolus of fluid may then be delivered or withdrawn from the catheter via the probe (210). The bolus may be delivered by the implantable infusion device to which the catheter is connected or may be delivered via a pressure monitoring system, such as a system depicted in and described with regard to FIGS. 7-10. The resulting intracatheter pressure may be monitored via an external pressure sensor to determine whether a pressure profile characteristic of a properly functioning catheter (220), an occluded catheter (240), or a catheter having an unintended leak (260) is observed or detected. If a pressure profile characteristic of a properly functioning catheter is observed or detected (220), a determination that no catheter malfunction exists can be made (230). If a pressure profile characteristic of an occluded catheter (240) or a leaky catheter (260) is observed or detected, a determination that a catheter malfunction exists can be made (250). If the results are inconclusive, the process or a portion thereof may be repeated.

As mentioned above, another way to determine the status of a catheter of an implantable infusion device is to monitor intracatheter pressure for characteristic physiologic pressure changes of cerebral spinal fluid (CSF) in which the catheter is implanted. Examples of such methods are described in U.S. Patent Application Publication No. 2008/0243074A1, entitled CATHETER MALFUNCTION DETERMINATIONS USING PHYSIOLOGIC PRESSURE, published on Oct. 2, 2008, which patent application is hereby incorporated herein by reference in its entirety to the extent that it does not conflict with the present disclosure.

Figure 14:
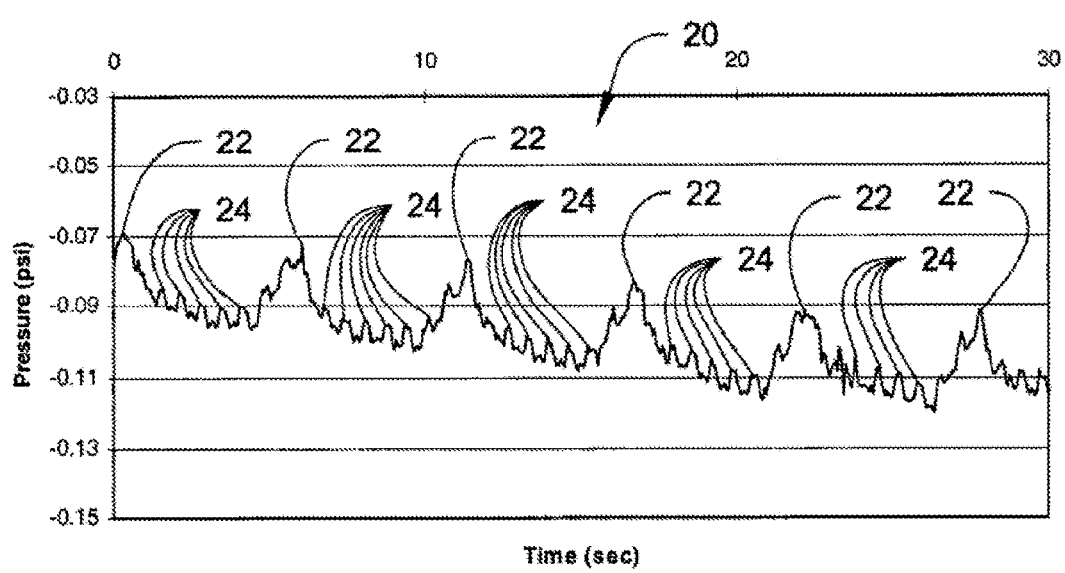
FIG. 14 is a graph of fluid pressure (y-axis) versus time (x-axis) in a catheter having an infusion section located in the CSF in the intrathecal space.

An example of a representative pressure profile of CSF in an animal, such as a sheep or dog, on mechanical ventilation is shown in FIG. 14. Pressure in the CSF has characteristic patterns that can be transmitted to a catheter in communication with the CSF, and thus through a probe and to an external pressure sensor. The data plotted in FIG. 14 demonstrates these patterns, where the plot 20 represents pressure of fluid within a lumen of a catheter located in fluid communication with the CSF. The pressure profile includes repeating major peaks 22 representative of patient respiration activity and repeating minor peaks 24 representative of cardiac activity (i.e., heartbeats). The major peaks 22 and minor peaks 24 are transmitted into the fluid in the lumen from the CSF (into which the lumen opens). The major peaks 22 repeat about every 2 to 10 seconds, which corresponds to about 30 to 6 breaths per minute. Typically, major peaks 22 repeat about every 3 to 5 seconds, which corresponds to about 20 to 12 breaths per minute. The amplitude of the major peaks 22 can vary (e.g., depending on the nature of the catheter), but are often less than 4 mmHg in amplitude, typically between about 1 mmHg and about 4 mmHg or between about 1 mmHg and 3 mmHg within a catheter such as Medtronic, Inc.'s Model 8709SC or 8731 SC silicone catheters with an inner diameter of about 0.53 mm.

The minor peaks 24 repeat about every half second to about every second and a half, which corresponds to about 40 to 120 heart beats per minute. Typically, the minor peaks 24 repeat about every 0.6 seconds to about every 1 second, corresponding to a heart rate of about 100 beats per minute to about 60 beats per minute. The amplitude of the minor peaks 24 can vary (e.g., depending on the nature of the catheter), but are often between about 0.5 mmHg and about 1 mmHg in amplitude within a catheter such as Medtronic, Inc.'s Model 8709SC or 8731 SC silicone catheters with an inner diameter of about 0.53 mm.

It should be noted that the pressure associated with respiration is exaggerated in cases where an animal is on mechanical ventilation (see. e.g, FIGS. 14, 16 and 18) relative to the free-breathing animal. Accordingly, the differences in amplitude of the peaks corresponding to respiration (major peaks) and heart rate (minor peaks) may not be as discernible in a free-breathing animal or human. It will be understood pressure changes that generally repeat in coordination with the animal's or patient's breathing or heart rate may be detected, regardless of the amplitude. In some instances, it may be difficult to detect pressure changes associated with both breathing and heart rate. However, pressure changes in the CSF or other fluid filled compartment associated with one or the other of heart rate and respiration are typically detectable and are transmittable via a catheter having an infusion section opening into the compartment. In some embodiments, characteristic pressure changes associated with one or both of heart rate and respiration are detected to determine catheter status.

Although physiological pressure modulations may be caused by respiration and/or cardiac activity at the selected internal delivery site, other physiological pressure modulations may be caused by, e.g., changes in posture. For example, as a patient moves from a horizontal (e.g., supine, prone, etc.) position to an upright position, the spinal column of a human moves from a generally horizontal orientation to a generally vertical orientation. In response to such posture changes, the fluid head of the CSF within the intrathecal space will change. Fluid-head pressure modulations caused by posture changes will typically be greater towards the lower end of the spinal column due to the larger volume of CSF located above the lower end of the spinal column when the spinal column is generally vertical. Such physiological pressure modulations may be controlled by directing a patient to change posture and measuring/detecting the resulting pressure modulations.

Other physiologic parameters that can result in a CSF pressure change that can be detected via a pressure monitoring system as described herein include pressure changes due to a patient coughing or performing a valsalva maneuver (forceable exhalation against a closed airway that can be done by closing one's mouth and pinching one's nose shut).

Figure 15:
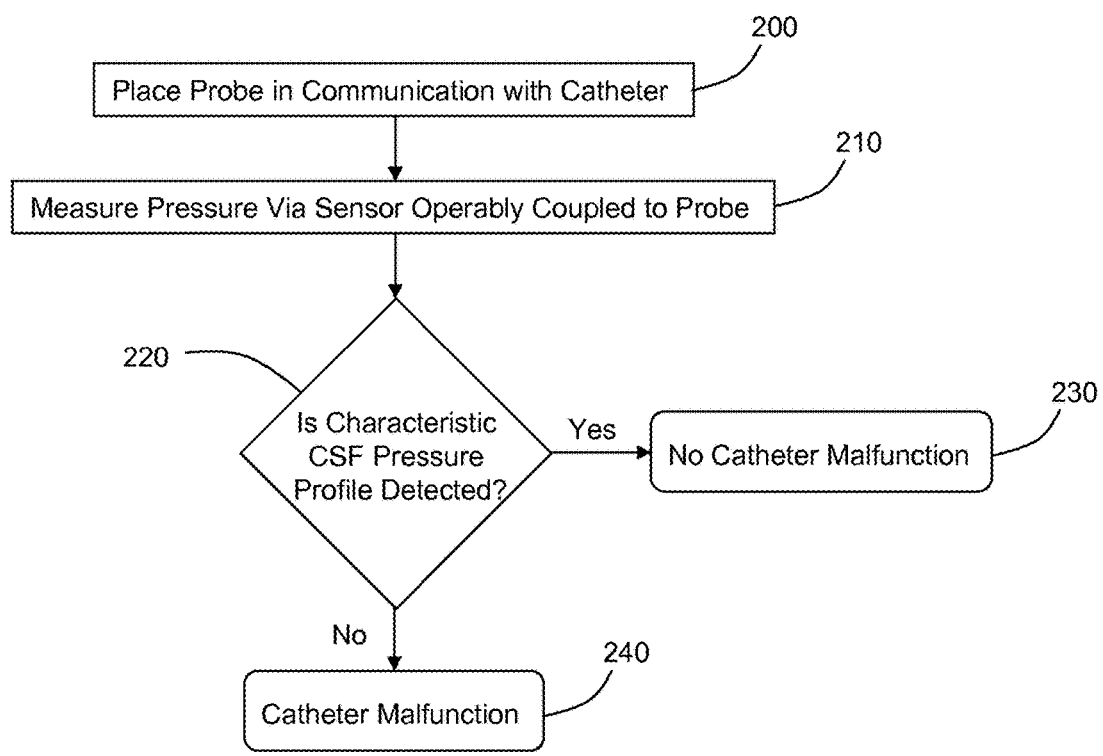
FIG. 15 is a flow diagram providing an overview of an embodiment of a method described herein.

The method depicted in FIG. 15 may be carried out using an external pressure sensor operably coupled to a probe that can placed in communication with an implanted catheter, e.g. via a port, such as a catheter access port, in fluid communication with the catheter. The method includes placing the probe in communication with the catheter (200) and measuring pressure via the pressure sensor operably coupled to the probe (210). A pressure profile may be developed based on the measured pressure and a determination can be made as to whether the pressure profile is characteristic of a CSF pressure profile (e.g., as shown in, and discussed with regard to, FIG. 14, as produced by a posture change, a cough, a valsalva maneuver, or the like). If the developed profile based on the measured pressure is characteristic of a CSF pressure profile, a determination may be made that the catheter is functioning properly (230).

While much of the description provided above related to monitoring pressure changes in the CSF due to physiologic parameters, it will be understood that many similar pressure changes can be observed in other fluid filled compartments of a patient, such as a patient's vasculature. Accordingly, the teachings present herein may be readily applied to monitoring intracatheter pressure changes due to physiological parameters, where the catheter has an opening in the patient's vascular system. Determinations as to whether an occlusion or leak exists in a catheter having a delivery region implanted in a patient's artery, vein or the like may be performed in a manner similar to that described above with regard to a catheter having a delivery region implanted in the CSF.

Further, it will be understood that the bolus pressure profiles as described herein (e.g., as described with regard to FIGS. 11-13) can be effectively monitored regardless of where the catheter is intended to deliver fluid. That is, such bolus pressure profiles can be detected in catheters having a delivery region implanted in the patient's CSF, vasculature, solid tissue, or at any other location in the patient.

Whether a characteristic pressure profile following delivery or withdrawal of a bolus or associated with a physiological parameter is used to determine the status of an implanted catheter, characteristic pressure patterns, shapes, or profiles may be used to identify catheter malfunctions. Pressure modulation profiles may be developed based on monitored pressure and compared to predetermined pressure profiles, such as predetermined intracatheter bolus pressure profiles or predetermined physiologic profiles, for determining the status of the catheter. Predetermined pressure profiles may be generated based on empirical measurements within an individual, a group of individuals or populations. The predetermined profiles may be averaged within or between individuals or groups. The predetermined profiles may be generated based on pressure measured within a fluid filled compartment, such as the CSF, within a catheter opening into the fluid filled compartment, or the like. In some embodiments, predetermined pressure profiles are generated, at least in part, on theoretical considerations. For example, a pattern with rising and falling pressures repeating every two to ten seconds in conjunction with a patient's breathing pattern can be considered a predetermined pressure profile correlating to respiration without any empirical data. Predetermined pressure profiles for bolus delivery and withdrawal may likewise be determined based on known compliance and resistance of a given catheter or catheter type, by empirical test within a patient or sample of patients, by bench test characterization, or by purely theoretical considerations. The pressure measurements in FIGS. 11, 12 and 14 depict pressure measurements as a function of time to illustrate the principles described herein. It should be understood that these pressure curves are presented as non-limiting examples. Although scales may be included, the systems and methods described herein are not limited to catheters in which these same pressures are developed. Rather, the profiles, shapes or patterns of the pressure curves may be used to identify catheter malfunctions in connection with the methods and systems presented herein.

Depending on the characteristic pressure profile monitored, the methods described herein may involve a variety of different analyses. Potential analytical methods may include, e.g., direct observation of the pressure modulation profile (e.g., on a display), comparison of the pressure modulation profile to a selected pressure profile (using, e.g., a look-up table, etc.), etc. In some methods, the physiological events that impact the pressure modulation profile may be tracked and correlated to changes in the pressure modulation profile (e.g., heart rate may be monitored, respiration may be monitored (using, e.g., thoracic impedance, etc.). In some embodiments, analytical methods to measure, for example, p-p amplitude in frequency band of interest may be used.

If it is determined that a catheter malfunction exists, a variety of actions may be taken. For example, the delivery of fluid through the catheter may be terminated; the rate of delivery of the fluid may be changed, etc.

While most of the discussion presented above was with regard to determining the status of a catheter in an implantable infusion system, it will be understood that the teachings presented herein may be readily applied to other systems employing implanted catheters. By way of example, the status of a catheter of a shunt system may be monitored via an external pressure sensor in accordance with the teachings presented herein. Many shunt systems include a catheter positioned in a cerebral ventricle with a port implanted in or near the skull. The port is in fluid communication with the catheter, and thus with the CSF of the ventricle. A probe can transcutaneously access the port, and a pressure sensor coupled to the port can be used to monitor intracatheter pressure, e.g. as described above with regard to an implantable infusion system, to determine whether the catheter is properly functioning or occluded.

In the following, non-limiting Examples are provided of systems and methods for monitoring intracatheter pressure via a pressure sensor operably coupled to a probe transcutaneously placed in fluid communication with an implanted catheter.

EXAMPLES

Figure 16:
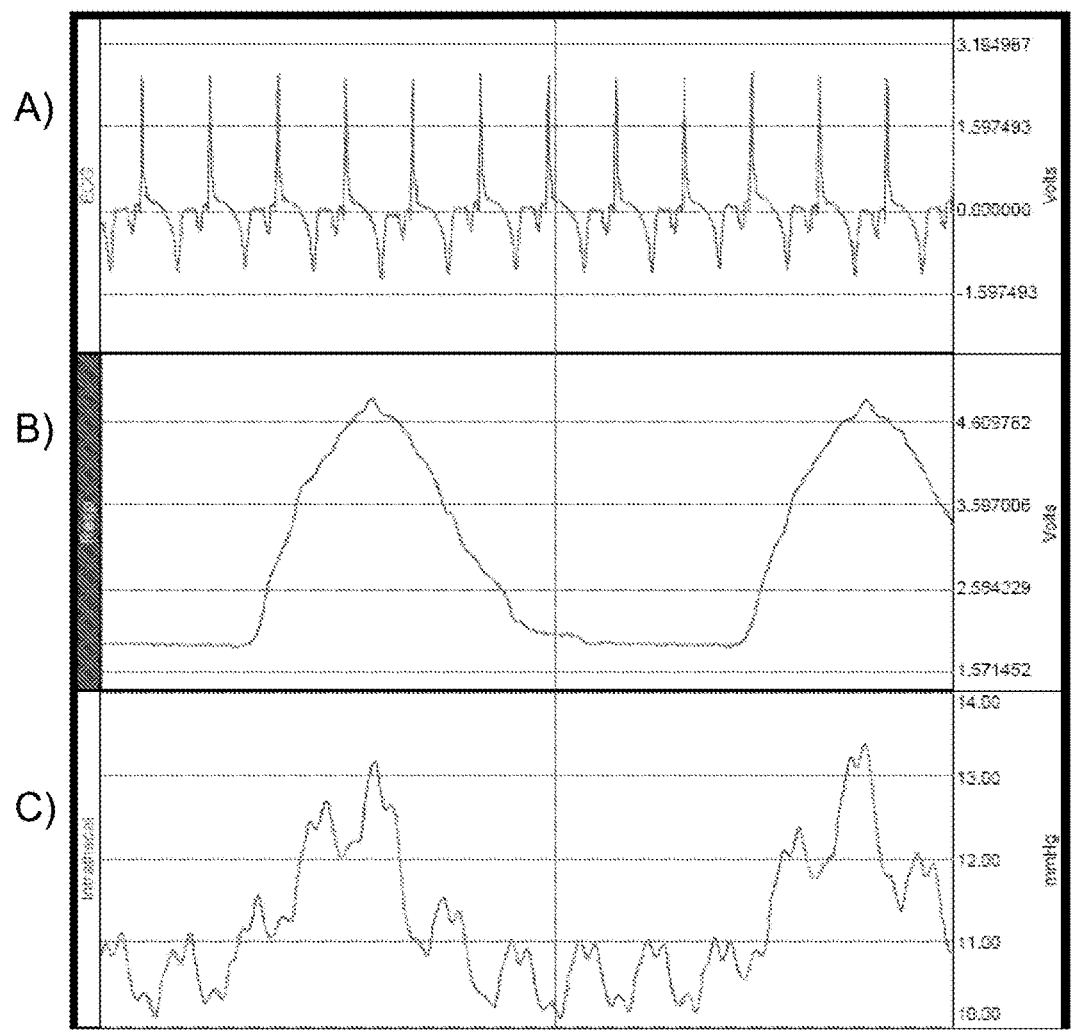
FIG. 16 is a graph of cardiac activity (A), respiration activity (B) and fluid pressure in a catheter having an infusion section located in the CSF in the intrathecal space (C) versus time obtained from an anesthetized sheep on a ventilator.
Figure 17:
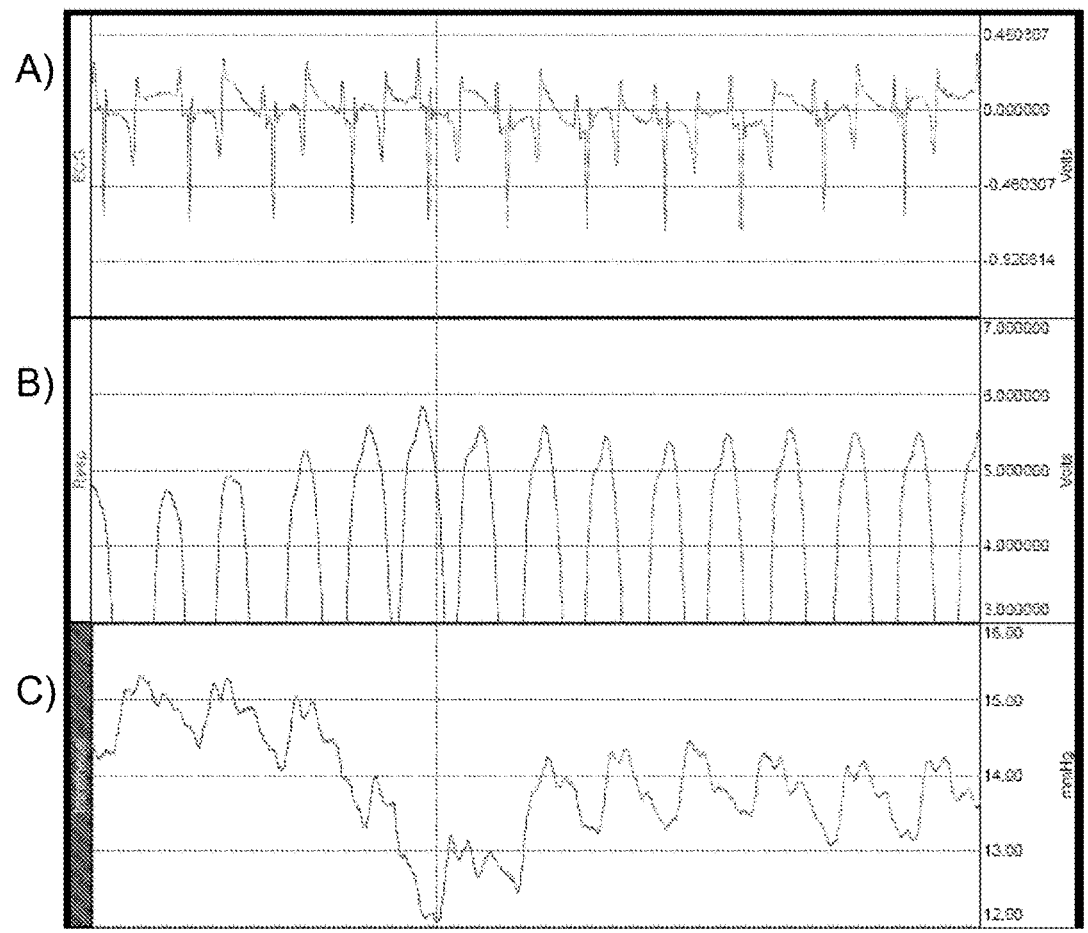
FIG. 17 is a graph of cardiac activity (A), respiration activity (B) and fluid pressure in a catheter having an infusion section located in the CSF in the intrathecal space (C) versus time obtained from sheep supported by a sling.

Example 1: Monitoring of Intracatheter Pressure of a Catheter Implanted in a Sheep Via an External Monitoring System A sheep was anesthetized and a Medtronic, Inc. Model 8709 one-piece intrathecal catheter was introduced into the intrathecal space via a lumbar puncture and advanced to T6 under fluoroscopic monitoring. The extraspinal portion of the catheter was tunneled subcutaneously to between the shoulder blades and externalized through stab incisions. The catheter was anchored securely to the skin after closure of the surgical incision. A twenty three gauge needle was attached to the externalized catheter to provide a connection to a pressure transducer (Hospira TransPac IV, Hospira, Inc,). Transducer signals were conditioned through BioPac DA 100C amplifiers (Biopac Systems, Inc.) with the gain set to 5000, bandwidth of 300 Hz, at a 16-bit sample rate of 200 Hz. Intrathecal pressure, via the catheter, ECG, and respiration activity were monitored. FIGS. 16-17 show plots of cardiac activity (A, ECG), respiration activity (B), and intrathecal pressure (C) in the anesthetized sheep on a ventilator (FIG. 16) and the same sheep awake and supported by a sling (FIG. 17). As shown in the data plotted in FIGS. 16-17, the intrathecal catheter pressure profile is a composite of the respiration activity (respiration rate) and cardiac activity (heart rate).

Figure 18:
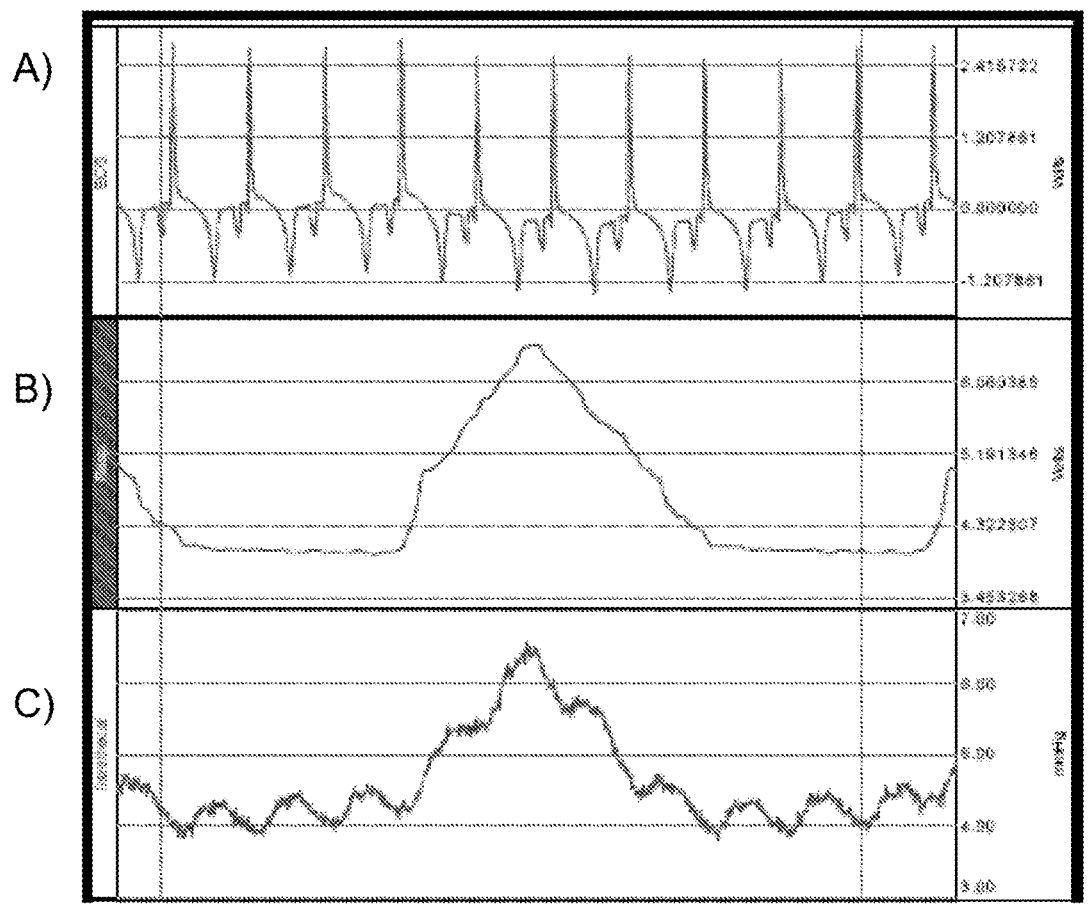
FIG. 18 is a graph of cardiac activity (A), respiration activity (B) and fluid pressure in a catheter having an infusion section located in the CSF in the intrathecal space (C) versus time obtained from a sheep. The fluid pressure was obtained from a catheter access port of an infusion device coupled to the catheter external to the sheep.

Referring now to FIG. 18, a plot of ECG activity, respiratory activity and intrathecal pressure in the same sheep as described with regard FIGS. 16-17 above is shown. The data presented in FIG. 18 regarding the intrathecal pressure were obtained from a catheter access port of a SynchroMed II infusion device (Medtronic, Inc.) coupled to the externalized catheter, while the sheep was under anesthesia and on a ventilator. To obtain the pressure signal, a 24 gauge Huber needle connected to a pressure transducer via a short length of fluid filled tubing was inserted into the catheter access port. As in FIGS. 16-17, the intrathecal pressure profile (C) depicted in FIG. 18 reflects a composite of respiration activity (B) and cardiac activity (A), with major peaks corresponding to respiration rate and minor peaks corresponding to heart rate. While the pressure waveforms in FIG. 18 are discernible, they are attenuated or dampened relative to those shown in FIGS. 16-17. Nonetheless, the data presented in FIG. 18 shows that it is possible to monitor the pressure in a catheter that opens into cerebrospinal fluid space via a catheter access port of an implantable medical device.

Figure 19:
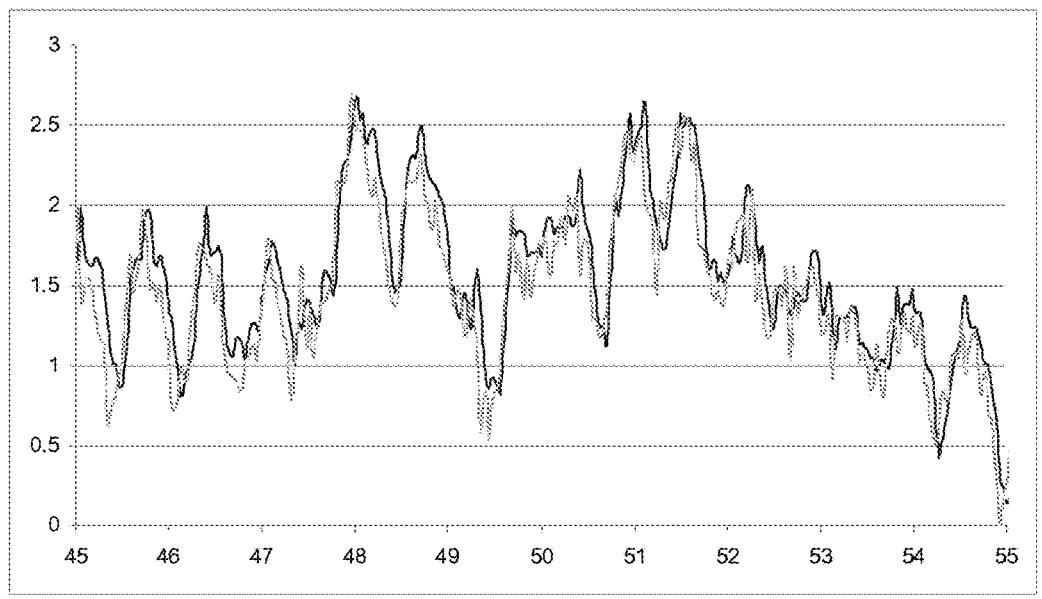
FIG. 19 is a graph of fluid pressure in mmHg (y-axis) in catheters versus time in seconds (x-axis) obtained (i) from a pressure sensor on-board an implantable infusion device, which on-board sensor was configured to measure intracatheter pressure, and (ii) from a pressure sensor in communication with a catheter via a probe inserted into a catheter access port of an implantable infusion device. The pressure was generated to mimic CSF fluid pressures measured in a sheep.
Figure 20:
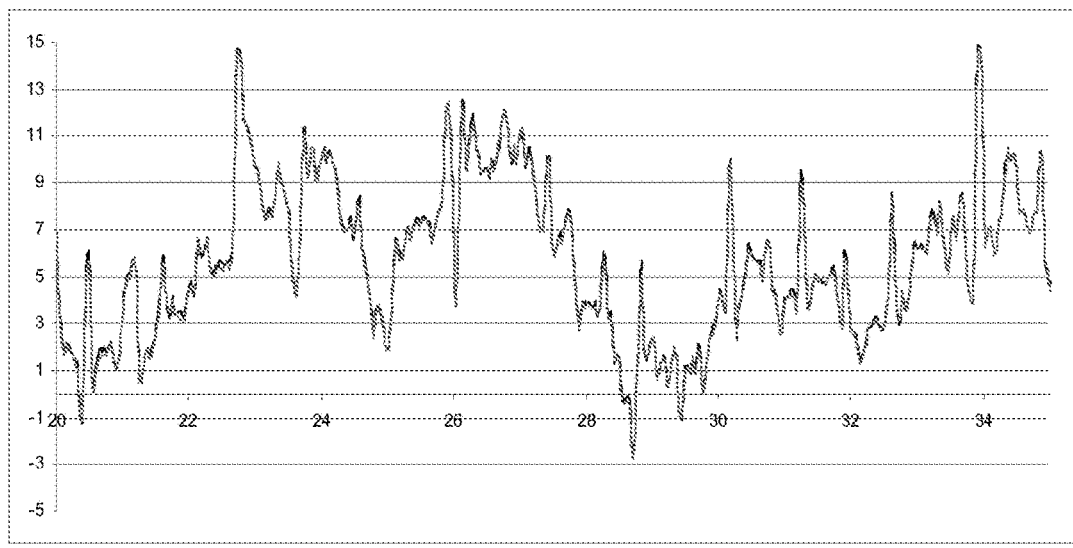
FIG. 20 is a graph of fluid pressure in mmHg (y-axis) in catheters versus time in seconds (x-axis) obtained (i) from a pressure sensor on-board an implantable infusion device, which on-board sensor was configured to measure intracatheter pressure, and (ii) from a pressure sensor in communication with a catheter via a probe inserted into a catheter access port of an implantable infusion device. The pressure was generated to mimic CSF fluid pressures measured in a sheep.

Example 2: Monitoring of Intracatheter Pressure of a Catheter in an Artificial System Via an External Monitoring System Referring now to FIGS. 19-20, plots are shown of pressure measured via (i) a pressure transducer in communication with a catheter and incorporated into an implantable medical device and (ii) a pressure transducer in communication with a catheter via a catheter access port of a SynchroMed II infusion device (Medtronic, Inc.). A 24-gauge needle was inserted into the catheter access port and coupled to the pressure transducer via a short length of fluid filled tubing. In both cases, the catheters were placed in fluid communication with an artificial source designed to reproduce CSF pressure recorded in resting sheep (FIG. 19) and sheep on a treadmill (FIG. 20). The pressure traces measured by both the pressure transducer incorporated into the infusion device and the pressure transducer coupled to the needle inserted in the catheter access port are shown in both FIG. 19 and FIG. 20. Because the measured pressure profiles are nearly identical, it is difficult to discern the difference between the two traces. The data presented in FIGS. 19-20 illustrate that catheter pressure can be monitored via an external pressure transducer in communication with the catheter via a needle inserted into a port in communication with the catheter (the catheter access port of a SynchroMed II infusion device) as well as pressure can be monitored via a pressure sensor on-board an implantable infusion device.

Figure 21:
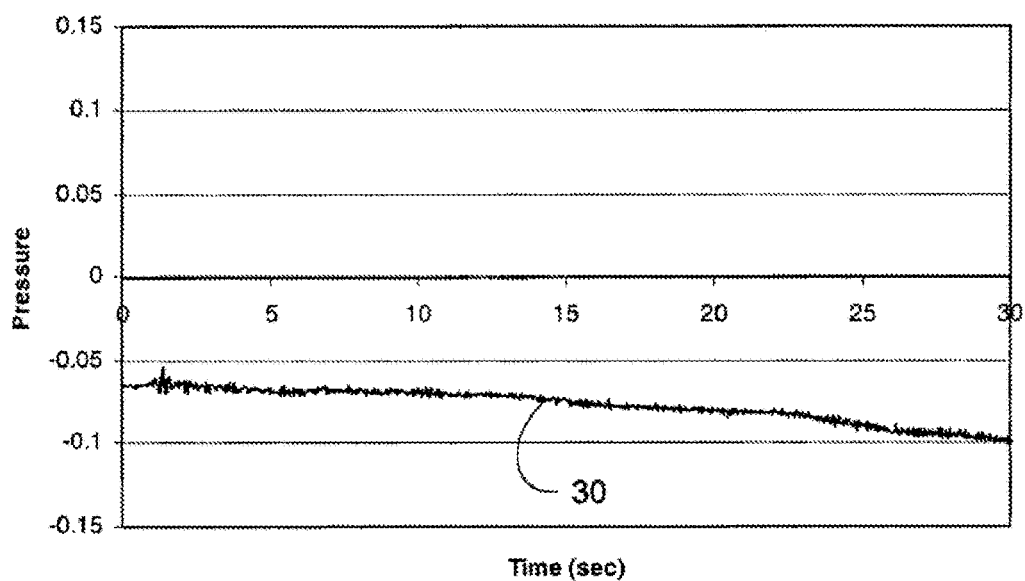
FIG. 21 is a graph of fluid pressure (y-axis) versus time (x-axis) in a catheter having an infusion section located outside the CSF.

Example 3: Monitoring of Intracatheter Pressure Via an External Monitoring System, Where the Catheter is Positioned Outside the CSF For purposes of comparison and with reference to FIG. 21, a plot demonstrating the pressure recorded within the fluid of a lumen of a catheter when the opening (e.g., infusion section) of the lumen is located outside of the intrathecal space is shown. As seen in plot 30 of FIG. 21, the pressure profile of the fluid located within the lumen when the opening is located outside of the intrathecal space is not noticeably modulated by physiological activity (such as, e.g., respiration or cardiac activity). It is theorized that the interstitial fluid pressure, i.e., the fluid pressure within the body but outside of any enclosed system (e.g. fluid-filled space (such as a blood vessel, intrathecal space, etc.), in an organ, etc.) is relatively constant throughout the body. When a catheter lumen opens within this interstitial space, significant pressure modulations are not typically observed in the lumen, with the resulting pressure modulation profile appearing similar to that depicted in FIG. 21. Pressure modulation profiles for catheters that are blocked or are leaking within the interstitial space will also not typically include modulations indicative of physiological pressure modulations. It should be noted that if the catheter has a leak at a location within the CSF, a characteristic CSF pressure profile may be detected with in the catheter, but the catheter may be delivering therapeutic agent to an undesired location within the CSF.

Those skilled in the art will recognize that the preferred embodiments may be altered or amended without departing from the true spirit and scope of the disclosure, as defined in the accompanying claims.

What is claimed is:

1. A system for determining whether an implanted infusion system has catheter complications, the implantable infusion system comprising a catheter access port in communication with a lumen of a catheter, the lumen of the catheter having an inner diameter defined by the lumen, the system comprising:
a probe having a lumen defining an inner diameter, wherein the inner diameter of the probe is less than or equal to 60% of the inner diameter of the catheter, wherein the probe is configured to be percutaneously inserted into the catheter access port;
a pressure sensor operably coupled to the probe and configured to measure pressure in the lumen of the probe; and
a processor configured to identify pressure changes associated with a physiological event by comparing pressure measured via the pressure sensor to a pressure profile associated with the physiological event.

2. A system according to claim 1, further comprising a tube operably coupled to the probe, the tube having a lumen defining an inner diameter, wherein the inner diameter of the probe is less than or equal to 60% of the inner diameter of the tube.

3. A system according to claim 1, further comprising a monitor configured to display a representation of pressure measured by the pressure sensor.

4. A system according to claim 1, further comprising a bolus delivery apparatus configured to deliver or withdraw a bolus of fluid through the lumen of the probe.

5. A system according to claim 4, wherein the processor is configured to compare pressure measured via the pressure sensor to a predetermined bolus pressure profile for the catheter.

6. A system according to claim 5, wherein the processor is configured to determine that the catheter is occluded if a developed bolus pressure modulation profile has a pressure decay rate slower than the predetermined bolus pressure profile.

7. A system according to claim 5, wherein the processor is configured to determine that the catheter has a leak if a developed bolus pressure modulation profile has a pressure decay rate faster than the predetermined bolus pressure profile.

8. A system according to claim 1, the pressure profile associated with the physiological event comprising one or both of (i) a peak corresponding to the patient's respiratory activity and (ii) a peak corresponding to the patient's cardiac activity.

9. A system according to claim 8, wherein the pressure profile associated with the physiological event comprises a plurality of peaks that repeat every two to ten seconds, corresponding to the patient's respiratory rate, and a plurality of peaks that repeat every half second to second and a half, corresponding to the patient's cardiac activity.

10. A system according to claim 8, wherein the processor is configured to determine that a catheter complication exists if a profile of pressure measured via the pressure sensor does not exhibit a predetermined characteristic of the pressure profile associated with the physiological event.

11. A system according to claim 1, wherein the pressure profile associated with the physiological event comprises a cough or a Valsalva maneuver.

12. A system according to claim 1, wherein the probe comprises a 24 or higher gauge needle.

13. A system for determining whether an implanted infusion system has catheter complications, the implantable infusion system comprising a catheter access port in communication with a lumen of a catheter, the system comprising:
a probe configured to be percutaneously inserted into the catheter access port;
a pressure sensor operably coupled to the probe and configured to measure pressure in the lumen of the probe; and
a processor configured to identify pressure changes associated with a physiological event by comparing pressure measured via the pressure sensor to a pressure profile associated with the physiological event.

14. A system according to claim 13, further comprising a bolus delivery apparatus configured to deliver or withdraw a bolus of fluid through the lumen of the probe.

15. A system according to claim 14, wherein the processor is configured to compare pressure measured via the pressure sensor to a predetermined bolus pressure profile for the catheter.

16. A system according to claim 15, wherein the processor is configured to determine that the catheter is occluded if a developed bolus pressure modulation profile has a pressure decay rate slower than the predetermined bolus pressure profile.

17. A system according to claim 15, wherein the processor is configured to determine that the catheter has a leak if a developed bolus pressure modulation profile has a pressure decay rate faster than the predetermined bolus pressure profile.

18. A system according to claim 13, the pressure profile associated with the physiological event comprising one or both of (i) a peak corresponding to the patient's respiratory activity and (ii) a peak corresponding to the patient's cardiac activity.

19. A system according to claim 18, wherein the processor is configured to determine that a catheter complication exists if a profile of pressure measured via the pressure sensor does not exhibit a predetermined characteristic of the pressure profile associated with the physiological event.

20. A system according to claim 13, wherein the pressure profile associated with the physiological event comprises a cough or a Valsalva maneuver.

\* \* \* \* \*